United States Patent
McAlpine et al.

(10) Patent No.: US 11,820,061 B2
(45) Date of Patent: Nov. 21, 2023

(54) ADDITIVELY MANUFACTURED SELF-SUPPORTING MICROFLUIDICS

(71) Applicants: Regents of the University of Minnesota, Minneapolis, MN (US); U.S. Government as Represented by the Secretary of the Army, Washington, DC (US)

(72) Inventors: Michael C. McAlpine, Minneapolis, MN (US); Ruitao Su, Minneapolis, MN (US); Steven J. Koester, Edina, MN (US); Joshua Uzarski, Boston, MA (US)

(73) Assignees: Regents of the University of Minnesota, Minneapolis, MN (US); U.S. Government as Represented by the Secretary of the Army, Natick, MA (US)

( * ) Notice: Subject to any disclaimer, the term of this patent is extended or adjusted under 35 U.S.C. 154(b) by 0 days.

(21) Appl. No.: 16/951,794

(22) Filed: Nov. 18, 2020

(65) Prior Publication Data
US 2022/0072753 A1 Mar. 10, 2022

Related U.S. Application Data
(60) Provisional application No. 63/076,673, filed on Sep. 10, 2020.

(51) Int. Cl.
*B29C 48/05* (2019.01)
*B01F 33/30* (2022.01)
(Continued)

(52) U.S. Cl.
CPC .......... *B29C 48/05* (2019.02); *B29C 35/0805* (2013.01); *B29C 48/30* (2019.02);
(Continued)

(58) Field of Classification Search
CPC ..... B29C 48/05; B29C 48/30; B29C 35/0805; B33Y 30/00; B33Y 80/00; C08L 83/04
See application file for complete search history.

(56) References Cited

U.S. PATENT DOCUMENTS

| | | | |
|---|---|---|---|
| 6,401,001 B1 | 6/2002 | Jang et al. | |
| 6,509,085 B1 | 1/2003 | Kennedy | |

(Continued)

FOREIGN PATENT DOCUMENTS

| | | | |
|---|---|---|---|
| EP | 2705942 A1 | 3/2014 | |
| FR | 3077763 A1 | 8/2019 | |

(Continued)

OTHER PUBLICATIONS

"Polyjet & Multijet Modeling (MJM)," from 3 Faktur retrieved from https://3faktur.com/en/3d- printing-materials-technologies/polyjet-3d-printing-technology-overview/#1486035768388-4184bc65-d700, on Aug. 19, 2021, 6 pp.

(Continued)

*Primary Examiner* — Joseph S Del Sole
*Assistant Examiner* — John Robitaille
(74) *Attorney, Agent, or Firm* — Shumaker & Sieffert, P.A.

(57) ABSTRACT

A printed structure including a plurality of overlying layers of elongate polymeric filaments stacked on a surface of a substrate. The elongate polymeric filaments are stacked on each other along their lengths to form a liquid impermeable, self-supporting wall. The liquid impermeable self-supporting wall forms a wall angle of about 30° to about 90° with respect to a plane of the surface of the substrate.

19 Claims, 17 Drawing Sheets

(51) Int. Cl.
| | |
|---|---|
| B01L 3/00 | (2006.01) |
| B33Y 30/00 | (2015.01) |
| B33Y 80/00 | (2015.01) |
| B29C 48/30 | (2019.01) |
| B29C 35/08 | (2006.01) |
| C08L 83/04 | (2006.01) |
| B33Y 70/00 | (2020.01) |

(52) U.S. Cl.
CPC .............. *B33Y 30/00* (2014.12); *B33Y 80/00* (2014.12); *C08L 83/04* (2013.01); *B01F 33/30* (2022.01); *B01L 3/502715* (2013.01); *B01L 3/502738* (2013.01); *B01L 2200/0689* (2013.01); *B01L 2300/0627* (2013.01); *B01L 2300/123* (2013.01); *B01L 2400/06* (2013.01); *B29C 2035/0827* (2013.01); *B29C 2791/002* (2013.01); *B29C 2948/92571* (2019.02); *B33Y 70/00* (2014.12)

(56) References Cited

U.S. PATENT DOCUMENTS

| | | | |
|---|---|---|---|
| 10,150,253 | B2 | 12/2018 | DeSimone et al. |
| 10,583,613 | B2 | 3/2020 | Bharti et al. |
| 10,597,545 | B2 | 3/2020 | Lewis et al. |
| 2014/0356585 | A1* | 12/2014 | Duoss ................. B32B 7/04 428/188 |
| 2015/0010461 | A1* | 1/2015 | Cronin ................. C07F 19/005 556/29 |
| 2016/0009029 | A1* | 1/2016 | Cohen ................. B29C 64/209 264/250 |
| 2016/0288414 | A1* | 10/2016 | Ozbolat ................. A61F 2/2875 |
| 2016/0311168 | A1* | 10/2016 | Gilligan ................. B29C 64/393 |
| 2020/0047399 | A1 | 2/2020 | Guvendiren et al. |

FOREIGN PATENT DOCUMENTS

| | | |
|---|---|---|
| KR | 20180102412 A | 9/2018 |
| WO | 2014126837 A2 | 8/2014 |
| WO | 2016145050 A1 | 9/2016 |

OTHER PUBLICATIONS

"Stereolithography: Everything You Need To Know About SLA 3D Printing," from 3D Sourced, retrieved from https://3dsourced.com/guides/stereolithograph-sla/ on Aug. 19, 2021, 18 pp.
"Technical Data Sheet LOCTITE® SI 595, Known as LOCTITE® Superflex® Clear RTV Silicone," from Henkel Corporation, Dec. 2013, 2 pp.
"What is Carbon Digital Light Synthesis?", from Carbon, Inc., retrieved from https://www.carbon3d.com/our-technology/ on Aug. 20, 2021, 15 pp.
Athanasiadis et al., "Direct Writing of Elastic Fibers with Optical, Electrical, and Microfluidic Functionality," Advanced Materials Technologies, vol. 4, No. 7, Mar. 2019, No. 18005659, 6 pp.
Au et al., "3D-printed microfluidic automation," Lab on a Chip, vol. 15, No. 8, Apr. 2015, 8 pp.
Bhattacharjee et al., "The upcoming 3D-printing revolution in microfluidics," Lab on a Chip, vol. 16, No. 10, Apr. 2016, 23 pp.
Bishop et al., "3D-Printed Fluidic Devices for Nanoparticle Preparation and Flow-Injection Amperometry Using Integrated Prussian Blue Nanoparticle-Modified Electrodes," Analytical Chemistry, vol. 87, No. 10, Apr. 2015, 7 pp.
Capel et al., "Design and additive manufacture for flow chemistry," Lab on a Chip, vol. 13, No. 23, Dec. 2013, 8 pp.
Chin et al., "Commercialization of microfluidic point-of-care diagnostic devices," Lab on a Chip, vol. 12, No. 12, Jun. 2012, 46 pp.
Ching et al., "Fabrication of Complex 3D Fluidic Networks via Modularized Stereolithography," Advanced Engineering Materials, vol. 22, No. 3, Nov. 2019, 7 pp.
Ching et al., "Fabrication of integrated microfluidic devices by direct ink writing (DIW) 3D printing," Sensors and Actuators B: Chemical, vol. 297, Jun. 2019, 9 pp.
Comina et al., "Low cost lab-on-a-chip prototyping with a consumer grade 3D printer," Lab on a Chip, vol. 14, No. 16, Aug. 2014, 5 pp.
Coulembier et al., "From controlled ring-opening polymerization to biodegradable aliphatic polyester: Especially poly(β-malic acid) derivatives," Progress in Polymer Science, vol. 31, No. 8, Aug. 2006, 25 pp.
DeSimone, J., "What if 3D printing was 100x faster?", from B&H Photo Video, Mar. 2015, retrieved from https://www.youtube.com/watch?time_continue=640&v=ihR9SX7dgRo&feature=emb_logo on Aug. 20, 2021, 3 pp.
Enders et al., "3D Plinted Microfluidic Mixers—A Comparative Study on Mixing Unit Performances," Small, vol. 15, No. 2, Jan. 2019, 9 pp.
Erkal et al., "3D printed microfluidic devices with integrated versatile and reusable electrodes," Lab on a Chip, vol. 14, No. 12, Jun. 2014, 19 pp.
Feng et al., "Active fluidic chip produced using 3D-printing for combinatorial therapeutic screening on liver tumor spheroid," Biosensors & Bioelectronics, vol. 151, No. 111966, Mar. 2020, 8 pp.
Gong et al., "High density 3D printed microfluidic valves, pumps, and multiplexers," Lab on a Chip, vol. 16, No. 13, Jul. 2016, 9 pp.
Grossi et al., "Electrical Impedance Spectroscopy (EIS) characterization of saline solutions with a low-cost portable measurement system," Engineering Science and Technology, an International Journal., vol. 22, No. 1, Feb. 2019, 7 pp.
Grover et al., "Monolithic membrane valves and diaphragm pumps for practical large-scale integration into glass microfluidic devices," Sensors and Actuators. B: Chemical, vol. 89, No. 3, Apr. 2003, 9 pp.
Hama et al., "Evolution of mixing in a microfluidic reverse-staggered herringbone micromixer," Microfluidics and Nanofluidics, vol. 22, No. 54, Apr. 2018, 14 pp.
Ho et al., "3D printed microfluidics for biological applications," Lab on a Chip, vol. 15, No. 18, Jul. 2015, 11 pp.
Huh et al., "Reconstituting Organ-Level Lung Functions on a Chip," Science, vol. 328, Jun. 2010, 7 pp.
Hwang et al., "Non-planar PDMS microfluidic channels and actuators: a review," Lab on a Chip, vol. 17, No. 23, Nov. 2017, 19 pp.
Jia et al., "Effect of wall roughness on performance of microchannel applied in microfluidic device," Microsystem Technologies vol. 25, No. 6, published Sep. 2018, Issued Jun. 2019, 13 pp.
Johnson et al., "3D Printed Anatomical Nerve Regeneration Pathways," Advanced Functional Materials, vol. 25, No. 39, Oct. 2015, 13 pp.
Johnson et al., "3D Printed Nervous System on a Chip," Lab on a Chip, vol. 16, No. 8, Jan. 2016, 8 pp.
Joung et al., "3D Printed Stem-Cell Derived Neural Progenitors Generate Spinal Cord Scaffolds," Advanced Functional Materials, vol. 28, No. 39, Sep. 2018, No. 1801850, 10 pp.
Kadimisetty et al., "3D-printed supercapacitor-powered electrochemiluminescent protein immunoarray," Biosensors and Bioelectronics, vol. 77, Mar. 2016, 6 pp.
Keating et al., "3D Printed Multimaterial Microfluidic Valve," PLoS One, vol. 11, No. 8, Aug. 2016, 12 pp.
Kim et al., "Integrated microfluidic-based sensor module for real-time measurement of temperature, conductivity, and salinity to monitor reverse osmosis," Desalination, vol. 317, May 2013, 9 pp.
Kim et al., "Soft lithography for microfluidics: a review," BioChip Journal, vol. 2, No. 1, Mar. 2008, 11 pp.
Kitson et al., "Configurable 3D-Printed millifluidic and microfluidic 'lab on a chip' reactionware devices," Lab on a Chip, vol. 12, No. 18, Jul. 2012, 5 pp.
Koh et al., "A soft, wearable microfluidic device for the capture, storage, and colorimetric sensing of sweat," Science Translational Medicine, vol. 8, No. 366, Nov. 2016, 13 pp.
Kudryashov et al., "Grey scale structures formation in SU-8 with e-beam and UV," Microelectronic Engineering, vol. 67-68, Jun. 2003, 6 pp.
Lao et al., "Self-Sealed Bionic Long Microchannels with Thin Walls and Designable Nanoholes Prepared by line-Contact Capillary-Force Assembly," Small, vol. 13, No. 23, Jun. 2017, 7 pp.

(56) References Cited

OTHER PUBLICATIONS

Lewis, J.A., "Direct Ink Writing of 3D Functional Materials," vol. 16, No. 17, Nov. 2006, 12 pp.
Li et al., "Desktop aligner for fabrication of multilayer microfluidic devices," Review of Scientific Instruments, vol. 86, No. 7, Jul. 2015, 9 pp.
Magalhaes et al., "Brief Overview on Bio-Based Adhesives and Sealants," Polymers, vol. 11, No. 10, Oct. 2019, 20 pp.
Melin et al., "Microfluidic Large-Scale Integration: The Evolution of Design Rules for Biological Automation," Annual Review of Biophysics and Biomolecular Structure, vol. 36, Jun. 2007, 19 pp.
Meng et al., "3D Bioprinted in Vitro Metastatic Models via Reconstruction of Tumor Microenvironments," Advanced Materials, vol. 31, No. 10, Mar. 2019, No. e1806899, 19 pp.
Miller et al., "Rapid casting of patterned vascular networks for perfusable engineered three-dimensional tissues," Nature Materials, vol. 11, No. 9, Jul. 2012, 7 pp.
Mukherjee et al., "Rapid Prototyping of Soft Lithography Masters for Microfluidic Devices Using Dry Film Photoresist in a Non-Cleanroom Setting," Micromachines, vol. 10, No. 3, Mar. 2019, 11 pp.
Müller et al., "Formulating Adhesives and Sealants—Chemistry, Physics and Applications," Vincentz Network, Hannover, Germany, Jan. 2010, 328 pp.
Naderi et al., "Digital Manufacturing for Microfluidics," Annual Review of Biomedical Engineering, vol. 21, Jun. 2019, 42 pp.
Nge et al., "Advances in Microfluidic Materials, Functions, Integration and Applications," Chemical Reviews, vol. 113, No. 4, Feb. 2013, 79 pp.
Ogilvie et al., "Reduction of surface roughness for optical quality microfluidic devices in PMMA and COC," Journal of Micromechanics and Microengineering, vol. 20, No. 6, May 2010, 8 pp.
Ostendorf et al., "Two-Photon Polymerization: A New Approach to Micromachining," Photonics Spectra, vol. 40, No. 10, Oct. 2006, 7 pp.
Parekh et al., "3D printing of liquid metals as fugitive inks for fabrication of 3D microfluidic channels," Lab on a Chip, vol. 16, No. 10, May 2016, 9 pp.
Park et al., "3D Printed Polymer Photodetectors," Advanced Materials, vol. 30, No. 40, No. e1803980, Aug. 2018, 15 pp.
Park et al., "Two-photon stereolithography for realizing ultraprecise three-dimension nano/microdevices," Laser & Photonics Review, vol. 3, No. 1-2, Feb. 2009, 11 pp.
Peters, R., "Nucleo-cytoplasmic flux and intracellular mobility in single hepatocytes measured by fluorescence microphotolysis," The EMBO Journal, vol. 3, No. 8, Aug. 1984, 6 pp.
Plevniak et al., "3D Printed Microfluidic Mixer for Point-of-Care Diagnosis of Anemia," 2016 38th Annual International Conference of the IEEE Engineering in Medicine and Biology Society (EMBC), Aug. 2016, 4 pp.
Ponan et al., "3D printing of interdigital sensor based conductive ABS for salt and sucrose concentration sensing," Journal of Physics: Conference Series, vol. 1380, Dec. 2019, 012129, 5 pp.
Qiu et al., "3D Printed Organ Models with Physical Properties of Tissue and Integrated Sensors," Advanced Materials Technologies, vol. 3, No. 3, Mar. 2018, No. 1700235, 9 pp.
Rafeie et al., "An easily fabricated three-dimensional threaded lemniscate-shaped micromixer for a wide range of flow rates," Biomicrofluidics, vol. 11, No. 1, Jan. 2017, No. 014108, 15 pp.
Rahimi et al., "Review on rubbers in medicine: natural, silicone and polyurethane rubbers," Plastics, Rubber and Composites, vol. 42, No. 6, Dec. 2013, 8 pp.
Rogers et al., "3D printed microfluidic devices with integrated valves," Biomicrofluidics, vol. 9, No. 1, 016501, Jan. 2015, 9 pp.
Saggiomo et al., "Simple 3D Printed Scaffold-Removal Method for the Fabrication of Intricate Microfluidic Devices," Advanced Science, vol. 2, No. 9, Sep. 2015, 5 pp.
Samiei et al., "A review of digital microfluidics as portable platforms for lab-on a-chip applications," Lab on a Chip, vol. 16, No. 13, Jul. 2016, 21 pp.
Schudel et al., "Microfluidic chip for combinatorial mixing and screening of assays," Lab on a Chip, vol. 9, No. 12, Mar. 2009, 5 pp.
Shallan et al., "Cost-Effective Three-Dimensional Printing of Visibly Transparent Microchips within Minutes," Analytical Chemistry, vol. 86, No. 6, Feb. 2014, 7 pp.
Singh et al., "3D printed conformal microfluidics for isolation and profiling of biomarkers from whole organs," Lab on a Chip, vol. 17, No. 15, Jun. 2017, 11 pp.
Sochol et al., "3D printed microfluidic circuitry via multijet-based additive manufacturing," Lab on a Chip, vol. 16, No. 4, Feb. 2016, 11 pp.
Sochol et al., "3D printed microfluidics and microelectronics," Microelectronic Engineering, vol. 189, Apr. 2018, 17 pp.
Stamp et al., "Exploring the Limits of Cell Adhesion under Shear Stress within Physiological Conditions and beyond on a Chip," Diagnostics, vol. 6, No. 4, Oct. 2016, 15 pp.
Su et al., "3D printed electronic materials and devices," Robotic Systems and Autonomous Platforms, Advances in Materials and Manufacturing, Chapter 13, 2019, 26 pp. (Applicant points out, in accordance with MPEP 609.04(a), that the year of publication, 2019, is sufficiently earlier than the effective U.S. filing date, so that the particular month of publication is not in issue.).
Su et al., "3D printed self-supporting elastomeric structures for multifunctional microfluidics," Science Advances, vol. 6, No. 41, Oct. 2020, 11 pp.
Su et al., "Chemiresistive graphene biosensor using antimicrobial peptide arrays and a 3_D printed microfluidic device," Conference Poster Presentation: 2019 Chemical and Biological Defense Science & Technology (CBDS&T) Conference, Nov. 2019, 1 pp.
Symes et al., "Integrated 3D-printed reactionware for chemical synthesis and analysis," Nature Chemistry, vol. 4, May 2012, 6 pp.
Tang et al., "Automated 3D-Printed Unibody Immunoarray for Chemiluminescence Detection of Cancer Biomarker Proteins," Lab on a Chip, vol. 17, No. 3, Jan. 2017, 13 pp.
Therriault et al., "Chaotic mixing in three-dimensional microvascular networks fabricated by direct-write assembly," Nature Materials, vol. 2, No. 4, Apr. 2003, 8 pp.
Thoresen et al., "Microfluidic Large-Scale Integration," Science, vol. 298, No. 5593, Oct. 2002, 5 pp.
Tumbleston et al., "Continuous liquid interface production of 3D objects," Science, vol. 347, No. 6228, Mar. 2015, 4 pp.
Unger et al., "Monolithic Microfabricated Valves and pumps by Multilayer Soft Lithography," Science, vol. 288, No. 5463, Apr. 2000, 4 pp.
Urrios et al., "3D-printing of transparent bio-microfluidic devices in PEG-DA," Lab on a Chip, vol. 16, No. 12, May 2016, 8 pp.
Walsh et al., "Enabling Microfluidics: from Clean Rooms to Makerspaces," Trends in Biotechnology, vol. 35, No. 5, May 2017, 10 pp.
Wang et al., "A microfluidic chip with double-sided herringbone microstructures for enhanced capture of rare tumor cells," Journal of Materials Chemistry B, vol. 5, No. 46, Dec. 2017, 7 pp.
Widodo et al., "The Effect of NaCl Concentration on the Ionic NaCl Solutions Electrical Impedance Value using Electrochemical Impedance Spectroscopy Methods,", The 8th Annual Basic Science International Conference, East Java, Indonesia, Mar. 2018, 7 pp.
Williams et al., "A practical guide to the staggered herringbone mixer," Lab on a Chip, vol. 8, No. 7, Jul 2008, 19 pp.
Wu et al., "Microfluidic sensing: state of the art fabrication and detection techniques," Journal of Biomedical Optics, vol. 16, No. 8, Aug. 2011, No. 080901, 12 pp.
Young et al., "Fundamentals of microfluidic cell culture in controlled microenvironments," Chemical Society Reviews, vol. 39, No. 3, Mar. 2010, 24 pp.
Zhu et al., "3D Printed Functional and Biological Materials on Moving Freeform Surfaces," Advanced Materials, vol. 30, No. 23, Jun. 2018, No. 1707495, 8 pp.
Invitation to Pay Additional Fees and, Where Applicable, Protest Fee from International Application No. PCT/US2020/061072, mailed May 26, 2021, 19 pp.
International Search Report and Written Opinion of International Application No. PCT/US2020/061072, dated Jul. 22, 2021, 27 pp.

(56) References Cited

OTHER PUBLICATIONS

International Preliminary Report on Patentability from International Application No. PCT/US2020/061072, dated Mar. 23, 2023, 16 pp.

* cited by examiner

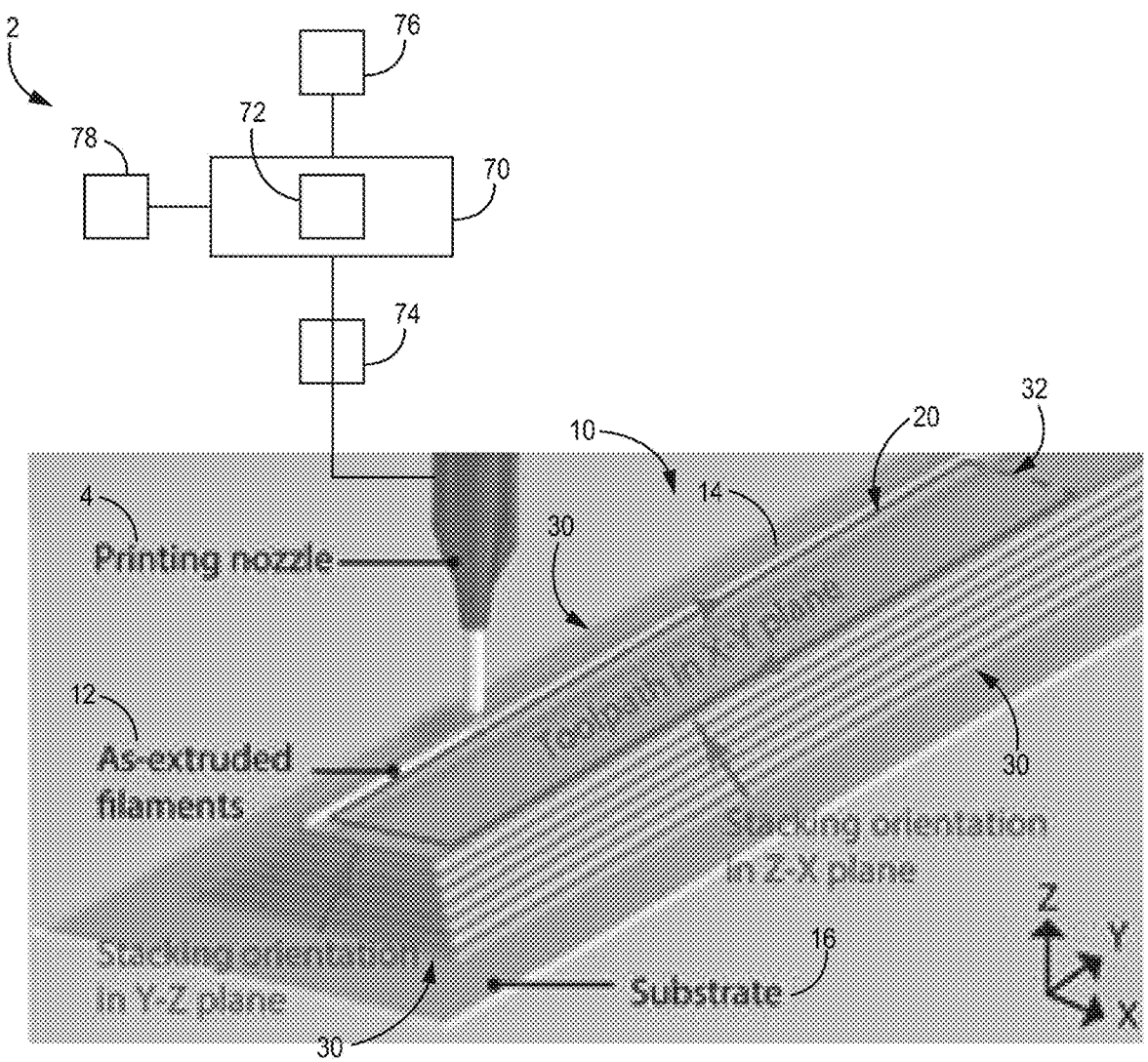
FIG. 1A-1
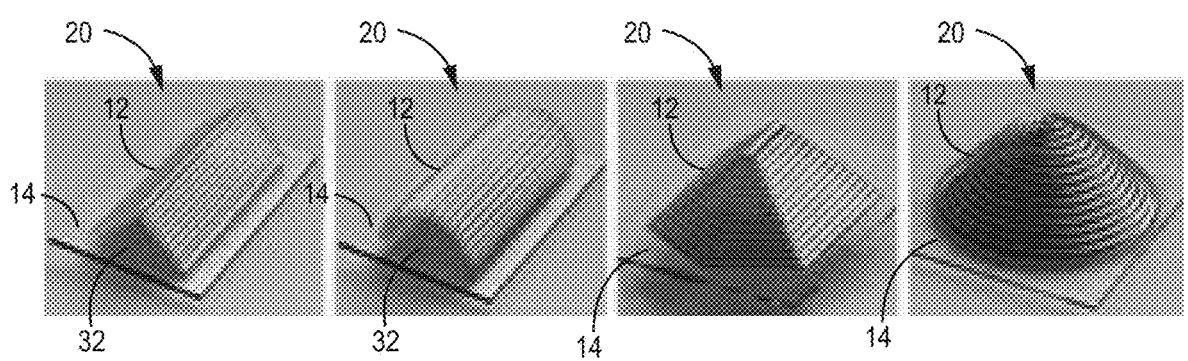
FIG. 1A-2  FIG. 1A-3  FIG. 1A-4  FIG. 1A-5

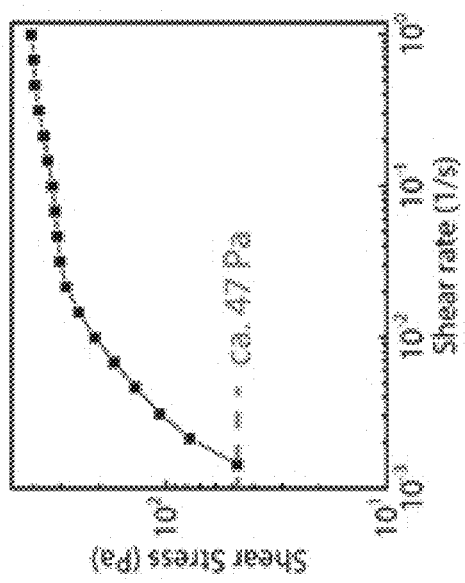
FIG. 1B-4
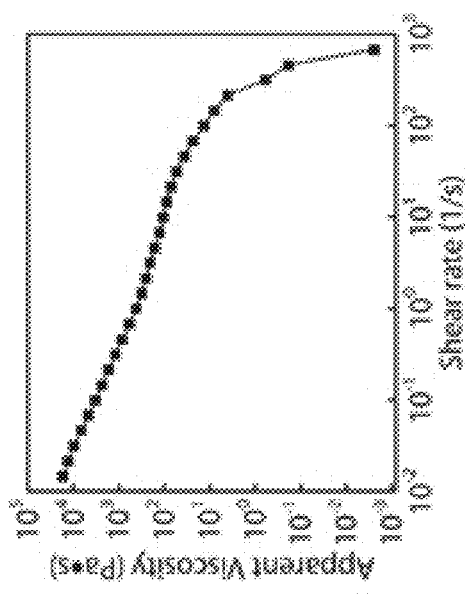
FIG. 1B-5
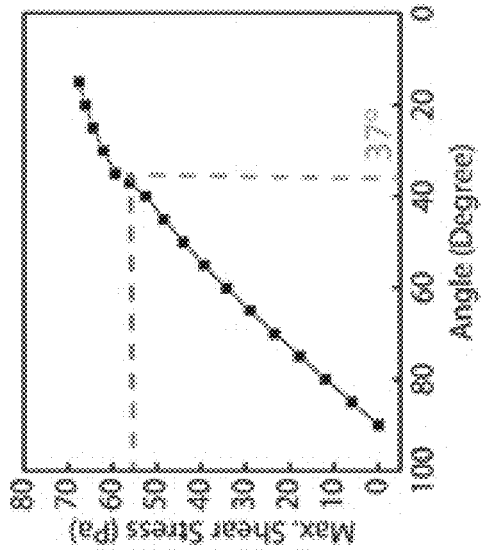
FIG. 1B-6
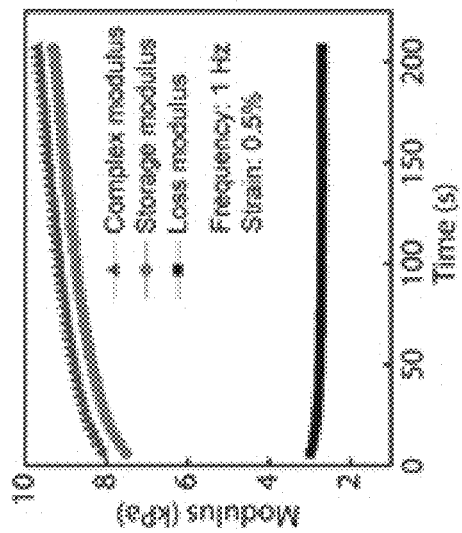
FIG. 1B-7
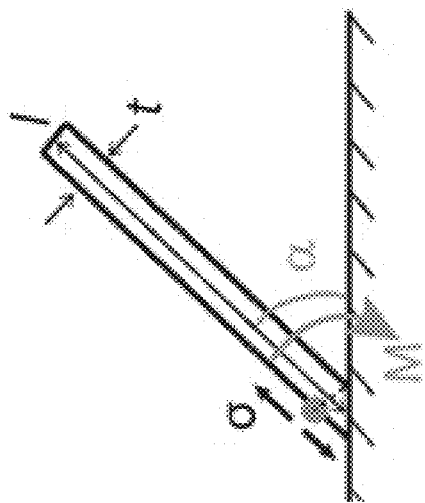
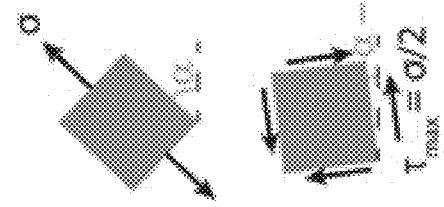
FIG. 1B-3

ADDITIVELY MANUFACTURED SELF-SUPPORTING MICROFLUIDICS

This application claims the benefit of U.S. Provisional Patent Application No. 63/076,673 filed Sep. 10, 2020, the entire content of which is incorporated herein by reference.

STATEMENT REGARDING FEDERALLY SPONSORED RESEARCH AND DEVELOPMENT

This invention was made with government support under Grant No. W911NF-18-2-0175 awarded by the Army Research Office; Grant No. EB020537 awarded by the National Institutes of Health; and Grant No. ECCS-1542202 awarded by the National Science Foundation. The government has certain rights in the invention.

BACKGROUND

Microfluidic devices, which have advantages of small sample volumes and well-controlled microenvironments, have the potential to enable transformational approaches for conducting microliter-scale chemical and biological research. For example, microfluidic devices have been used in areas such as lab-on-a-chip diagnostics, point-of-care systems, organ replication-on-a-chip, and bioassays. Currently available methodologies for the fabrication of microfluidic devices include soft lithography and additive manufacturing.

Soft lithography is a microfabrication-based method that can achieve sub-micron resolution in devices which are typically fabricated using the elastomer polydimethylsiloxane (PDMS). However, the requirement of microfabrication facilities, PDMS stamp distortions, as well as time-consuming manual steps such as PDMS molding, layer alignment and bonding, impose constraints on the use of soft lithography to produce ubiquitous and widely deployable microfluidic devices.

Additive manufacturing, or three-dimensional (3D) printing, techniques have also been used to make microfluidic devices. Comparative advantages of additive manufacturing techniques include the potential for autonomous and portable manufacturing, rapid prototyping and the ability to incorporate freeform 3D structures. Several 3D printing approaches have been used for the fabrication of microfluidic devices. Stereolithography (SL) is one extensively studied method that utilizes photo-curable resins to create well-defined microchannels with feature sizes below 100 μm and a range of components for fluid manipulation. Multi-jet modeling (MJM) fabricates microfluidic devices via inkjet printing UV-polymerizable inks and has the capability for printing multiple materials.

However, due to the potential for contamination from either uncured residual resin in the channel voids or the sacrificial supporting materials temporarily used to form hollow structures, directly printing microfluidic structures onto substrates that contain pre-deposited 3D structures or electronic sensing elements is challenging for SL and MJM. The degree of automation of SL and MJM is also compromised due to the necessary postprocessing to remove the residual precursor and supporting materials from the channels. In addition, microfluidic devices printed by SL and MJM with photo-curable resins have low elasticity and are difficult to align to existing structures.

SUMMARY

Extrusion-based 3D printing can provide a freeform method to fabricate objects via the conformal deposition of filaments onto target surfaces. However, without the support of added sacrificial materials, hollow structures directly printed with uncured viscoelastic inks have shown insufficient mechanical strength to counter the creep of the as-printed structures, which results in collapse of the hollow structures. While some hollow wall structures have been formed using 3D printing and then enclosed with a rigid and planar "roof" such as a glass slide, the use of such rigid materials can impose significant constraints on the overall resulting form factor of the printed device.

In one example, the present disclosure is directed to 3D printing techniques suitable for forming hollow structures in which at least one dimension of the hollow space is relatively small, for example, from several millimeters to several hundred micrometers (μm) to reduce total gravitational loading. The structures do not require sacrificial materials, and the viscosity of the polymeric material used to form the structures is suitable to ensure low resistance to extrusion and sufficient mechanical strength to balance the gravitational torque of an overhung part.

The automatable extrusion-based printing processes of the present disclosure can be used to directly align and print elastomeric microfluidic structures onto planar and non-planar substrates with minimal postprocessing. By selecting polymeric materials with a suitable yield strength and controlling the profiles of printed overhung structures, self-supporting walls can be formed from viscoelastic polymeric materials without the need to incorporate additional sacrificial materials. The as-printed self-supporting walls can withstand small bending moments and can be enclosed to form microfluidic devices having hollow structures such as channels and chambers without the need for non-polymeric roofs or other non-extrusion printed enclosing members.

In various embodiments, printing toolpaths can be used to form microfluidic structures having self-supporting and aligned enclosed fluid passages with leakage-free transitions between channels and chambers, T-shaped intersections and overlapping channels. For example, in various embodiments, the microfluidic structures can include multi-material mixers and microfluidic-integrated salinity sensors that are directly integrated with pre-deposited structures such as ridges, or may be aligned on a surface of a pre-fabricated sensor to overlie sensing microelectrodes. In other examples, the processes of the present disclosure may be used to 3D print microfluidic networks integrated with valves on a planar surface or a non-planar surface such as sphere. In one example, a microfluidic device 3D printed on a non-planar surface such as the human body can be used to make, for example, a wearable biochemical or health sensor.

In one aspect, the present disclosure is directed to a printed structure including a plurality of overlying layers of elongate polymeric filaments stacked on a surface of a substrate, wherein the elongate polymeric filaments are stacked on each other along their lengths to form a liquid impermeable, self-supporting wall. The liquid impermeable self-supporting wall forms a wall angle of about 30° to about 90° with respect to a plane of the surface of the substrate.

In another aspect, the present disclosure is directed to a printed structure that includes a plurality of overlying layers of elongate polymeric filaments stacked on a surface of a substrate. The elongate polymeric filaments are stacked on each other along their lengths to form opposed liquid impermeable, self-supporting walls each having a wall angle of greater than about 30° with respect to a plane of the surface of the substrate. The opposed liquid impermeable walls merge in an apex region to form an enclosed fluid passage.

In another aspect, the present disclosure is directed to a method of making a printed structure. The method includes extruding through a nozzle an elongate polymeric base filament in a pattern on a surface of a substrate, wherein the base filament has a length and a width; and moving the nozzle in a plane normal to a plane of the substrate to stepwise extrude and stack a plurality of polymeric filaments onto the base filament such that each of the polymeric filaments extruded onto the base filament contact one another along their lengths to form a wall with a wall angle of about 30° to about 90° with respect to the plane of the surface of the substrate.

In another aspect, the present disclosure is directed to a method of making a printed structure. The method includes extruding through a nozzle an elongate polymeric base filament in a pattern on a surface of a substrate, wherein the base filament has a length and a width; moving the nozzle in a first plane substantially normal to a plane of the substrate and a second plane substantially normal to the plane of the substrate to stepwise extrude and stack a plurality of polymeric filaments onto the base filament such that each of the polymeric filaments contact one another along their lengths to form opposed walls, wherein each of the opposed walls forms a wall angle of about 30° to about 90° with respect to a plane of the surface of the substrate; and moving the nozzle to extrude polymeric filaments to merge the walls to form an enclosed passage in the printed structure.

In another aspect, the present disclosure is directed to a microfluidic mixing device that includes a plurality of polymeric structures on a surface of a substrate, wherein the structures extend away from the surface of the substrate; a body, including an elongate polymeric base filament in a pattern on a surface of a substrate, wherein the base filament has a length and a width, and wherein a first portion the base filament at least partially bounds the plurality of polymeric structures, a plurality of polymeric filaments stacked onto the base filament such that each of the polymeric filaments contact one another along their lengths to form opposed first and second walls, wherein each of the first and the second opposed walls forms a wall angle of about 35° to about 90° with respect to a plane of the surface of the substrate, and a roof to connect the opposed first and second walls to form an enclosed fluid passage bounded by the opposed walls and the roof, wherein the fluid passage includes therewithin the plurality of structures.

In another aspect, the present disclosure is directed to a method for making a microfluidic mixing device. The method includes printing a plurality of polymeric structures on a surface of a substrate, wherein the structures extend away from the surface; printing an elongate polymeric base filament in a pattern on a surface of a substrate, wherein the base filament has a length and a width, and wherein a first portion the base filament at least partially bounds the plurality of polymeric structures; stacking a plurality of polymeric filaments onto the first portion of the base filament such that each of the polymeric filaments contact one another along their lengths to form opposed first and second walls, wherein each of the first and the second opposed walls forms a wall angle of about 35° to about 90° with respect to a plane of the surface of the substrate; and printing a roof to connect the opposed first and second walls to form an enclosed fluid passage bounded by the opposed walls and the roof, wherein the fluid passage includes therewithin the plurality of structures.

In another aspect, the present disclosure is directed to a method for making a microfluidic mixing device. The method includes printing a plurality of polymeric structures on a surface of a substrate, wherein the structures extend away from the surface; printing an elongate polymeric base filament in a pattern on a surface of a substrate, wherein the base filament has a length and a width, and wherein a first portion the base filament at least partially bounds the plurality of polymeric structures; stacking a plurality of polymeric filaments onto the first portion of the base filament such that each of the polymeric filaments contact one another along their lengths to form opposed first and second walls, wherein each of the first and the second opposed walls forms a wall angle of about 35° to about 90° with respect to a plane of the surface of the substrate; and printing a roof to connect the opposed first and second walls to form an enclosed fluid passage bounded by the opposed walls and the roof, wherein the fluid passage includes therewithin the plurality of structures.

In another aspect, the present disclosure is directed to a sensor system including a substrate having a sensor; and a printed structure comprising a plurality of overlying layers of elongate polymeric filaments stacked on a surface of the substrate proximal the sensor, wherein the elongate polymeric filaments are stacked on each other along their lengths to form opposed liquid impermeable walls each having a wall angle of greater than about 30° with respect to a plane of the surface of the substrate, and wherein the opposed liquid impermeable walls merge in an apex region to form an enclosed fluid passage, and wherein the fluid passage is in fluid communication with the sensor.

In another aspect, the present disclosure is directed to a method for making a sensor system. The method includes printing an elongate polymeric base filament in a pattern on the surface of a substrate, wherein the surface of the substrate includes a sensor with at least one electrode, wherein the base filament has a length and a width, and wherein a first portion the base filament at least partially bounds the sensor; stacking a plurality of polymeric filaments onto the first portion of the base filament such that each of the polymeric filaments contact one another along their lengths to form opposed first and second walls, wherein each of the first and the second opposed walls forms a wall angle of about 30° to about 90° with respect to a plane of the surface of the substrate; and printing a roof to connect the opposed first and second walls to form an enclosed fluid passage bounded by the opposed walls and the roof, wherein the fluid passage at least partially overlies the at least one electrode of the sensor.

In another aspect, the present disclosure is directed to valve including a flow channel having a plurality of overlying layers of elongate polymeric filaments stacked on a surface of a substrate, wherein the elongate polymeric filaments are stacked on each other along their lengths to form opposed liquid impermeable walls each having a wall angle of greater than about 35° with respect to a plane of the surface of the substrate, and wherein the opposed liquid impermeable walls merge in an apex region to form an enclosed fluid passage; a control channel including a plurality of overlying layers of elongate polymeric filaments stacked on each other along their lengths to form opposed liquid impermeable walls each having a wall angle of greater than about 35° with respect to a plane of the surface of the substrate, wherein the opposed liquid impermeable walls merge in an apex region to form an enclosed passage, and wherein the control channel includes a first portion on the surface of the substrate and a second portion that overlies the flow channel and forms an enclosed valve portion therebetween; and an encapsulant structure overlying the valve portion.

In another aspect, the present disclosure is directed to a three-dimensional printing system. The system includes an extruder that extrudes a polymeric material, wherein the extruder has a nozzle moved in response to instructions from a controller, and wherein the nozzle is configured to: move along a surface of a substrate to extrude an elongate polymeric base filament in a pattern on the surface of a substrate; move in a first plane substantially normal to a plane of the substrate and a second plane substantially normal to the plane of the substrate to stepwise form and stack a plurality of polymeric filaments onto the base filament such that each of the polymeric filaments contact one another along their lengths to form opposed walls, wherein each of the opposed walls forms a wall angle of about 30° to about 90° with respect to a plane of the surface of the substrate; and move in a region between the opposed walls to merge the walls to form a printed structure comprising an enclosed passage.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1A-1 is a schematic representation of a system and method for 3D printing a microfluidic channel.

FIG. 1A-2 is a 3D model of a self-supporting 3D printed structure including a fluid passage with a triangular cross-sectional shape.

FIG. 1A-3 is 2 is a 3D model of a self-supporting 3D printed structure including a fluid passage with a circular cross-sectional shape.

FIG. 1A-4 is a 3D model of a self-supporting 3D printed structure with a hexagonal domed shape.

FIG. 1A-5 is a 3D model of a self-supporting 3D printed structure with a conical domed shape.

FIGS. 1B-1 and 1B-2 are plots of a bending moment analysis of a self-supporting wall printed with a straight profile.

FIG. 1(B)(a)-1(B)(c) are composite cross-sectional images of silicone walls of varying incline angles and an overhang length of 700 μm, with scale bars of 200 μm.

FIG. 1B-3 is a diagram of a 3D printed wall showing the stress state of the wall root.

FIG. 1B-4 is a plot of predicted maximum shear stress at the wall root of FIG. 1B-3.

FIG. 1B-5 is a plot of the flow sweep of uncured room temperature vulcanizable (RTV) silicone, which increases as the material continuously cures in air.

FIG. 1B-6 is a plot showing that the storage modulus increases as RTV silicone cures in air.

FIG. 1B-7 is a plot showing that apparent viscosity of RTV silicone decreases with shear rate.

FIGS. 1C-1 to 1C-4 are photographs of 3D printed microfluidic channels and chambers with walls cut open to display the cross-sectional profiles, with 1 mm scale bars.

FIGS. 1D-1 and 1D-2 are scanning electron microscope (SEM) images of triangular and circular channels, respectively with a width of about 100 μm. The photographs have scale bars of 100 μm.

FIG. 2 is a schematic diagram of an embodiment of a 3D printed microfluidic mixer having integrated herringbone ridges.

FIG. 3 is a schematic overhead view of a 3D printed sensor including printed channels and chambers overlying sensor components on a chip.

FIG. 5 is a flow chart of an embodiment of a process for making a 3D printed microfluidic device according to the present disclosure.

Like symbols in the drawings indicate like elements.

DETAILED DESCRIPTION

Figures 1, 1B:
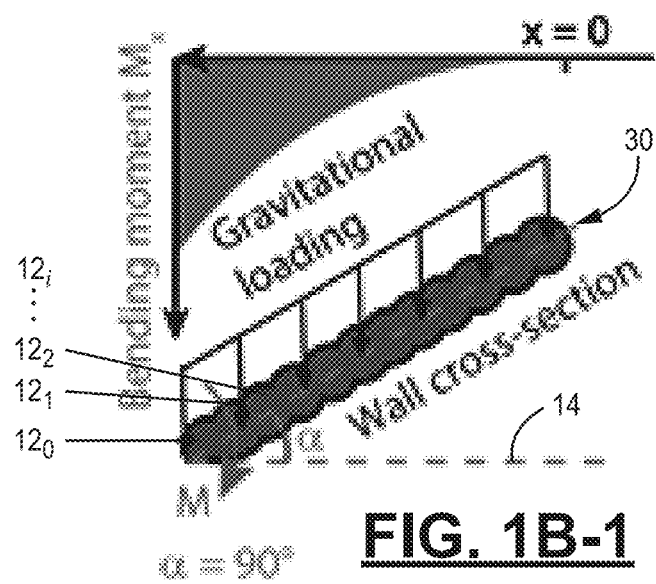

Referring now to FIG. 1A-1, a three-dimensional (3D) printing system 2 for extruding a 3D printed structure 10 is formed by extruding from a printing nozzle 4 an arrangement of overlying elongate polymeric filaments 12 on a surface 14 of a substrate 16.

In various examples shown schematically in FIG. 1A-1, the printing nozzle 4 in the system 2 may be interfaced with a controller 70 having at least one processor 72. The controller 70 may be configured to control one or more parameters of the printing nozzle 4 to determine one or more physical or chemical properties of the polymeric filaments 12 extruded from the nozzle 4. In some examples, which are not intended to be limiting, the controller 70 may be configured to mathematically reconstruct the surface geometry of a target surface, design routing and geometry of microfluidic channels based on the mathematical reconstruction of the surface geometry, to adjust one or more of the feed rate of a polymeric material to the printing nozzle 4, to adjust an angle of the printing nozzle 4 with respect to a plane of the surface 14, to form the toolpath of the printing nozzle 4 to create a desired pattern of the extruded polymeric material in the plane of the surface 14, or to move the printing nozzle 4 in one or more planes normal to the plane of the surface 14 to stack the filaments 12 on one another to form wall-like structures and enclosed passages.

In some examples, the controller 70 may be configured to process detected signals from one or more sensor systems 74 in or on the system 2. The processor 72 may be integrated with the sensor systems 74, may be integrated with the controller 70, or may be a remote processor functionally connected to the controller 70.

The processor 72 may be any suitable software, firmware, hardware, or combination thereof. The processor 72 may include any one or more microprocessors, controllers, digital signal processors (DSPs), application specific integrated circuits (ASICs), field-programmable gate arrays (FPGAs), or discrete logic circuitry. The functions attributed to the processor 72 may be provided by processing circuitry of a hardware device, e.g., as supported by software and/or firmware.

In some examples, the processor 72 may be coupled to a memory device 76, which may be part of the controller 70 or remote thereto. The memory device 76 may include any volatile or non-volatile media, such as a random-access memory (RAM), read only memory (ROM), non-volatile RAM (NVRAM), electrically erasable programmable ROM (EEPROM), flash memory, and the like. The memory device 76 may be a storage device or other non-transitory medium. The memory device 76 may be used by the processor 72 to, for example, store fiducial information or initialization information corresponding to, for example, surface geometries, microfluidic channel designs, measurements or stored signals from the sensor system 74 of parameters of the system 2, the filaments 12, and the structures 10 formed therefrom. In some examples, the memory device 76 may store determined values, such as information corresponding to detected viscosity measurements for the extruded polymeric material, extrusion rates, toolpath patterns, and the like, for later retrieval.

In some embodiments, the controller 70 and the processor 72 are coupled to a user interface 78, which may include a display, user input, and output (not shown in FIG. 1A-1). Suitable display devices include, for example, monitor, PDA, mobile phone, tablet computers, and the like. In some examples, user input may include components for interaction with a user, such as a keypad and a display such as a cathode ray tube (CRT) display, a liquid crystal display (LCD) or light emitting diode (LED) display, and the keypad may take the form of an alphanumeric keypad or a reduced set of keys associated with particular functions. In some examples, the displays may include a touch screen display, and a user may interact with user input via the touch screens of the displays. In some examples, the user may also interact with the user input remotely via a networked computing device.

The controller 70 can be configured to control any selected number of functions of the extrusion apparatus 2 including, but not limited to, toolpath patterns for the printing nozzle 4 considering channel width, filament diameter, wall incline angle, and overlapping of adjacent overlying filaments, extrusion rates for the polymeric materials extruded from the printing nozzle 4, and the like, in response to signals from the processor 72 input manually into the controller 70, or stored in the memory device 76. For example, in some embodiments, the controller may be used to mathematically reconstruct the target surface geometry and design the routing and geometry of microfluidic channels to incorporate pre-deposited elements, and to generate continuous and conformal printing toolpaths considering channel width, filament diameter, wall incline angle and overlapping of adjacent filaments. As will be discussed in more detail below, the controller 70 may also be used to print microstructures within the channels formed by the walls, encapsulate valves and pumps, and cut openings in the walls as need to insert connection tubes, and apply sealants to provide airtight or liquid-tight connections.

In some examples, the controller 70 can be configured to generate control signals obtained from, for example, one or more sensors in the sensor system 74, to provide closed loop control of the toolpath patterns and composition of the filaments 12 and the printed structure 10.

In various examples, the controller 70 may be adjusted by a variety of manual and automatic means. Automatic means may make use of any number of control algorithms or other strategies to achieve desired conformance to a control toolpath patterns or filament constructions for the printed structure 10. For example, standard control schemes as well as adaptive algorithms such as so-called "machine-learning" algorithms may be used. In some examples, controller 70 can utilize information from other sources such as, for example, infrared cameras, to determine the control action decided by algorithms such as PID control schemes or machine learning schemes.

The surface 14 in FIG. 1A-1 is substantially planar, but in some embodiments may be non-planar such as for example, arcuate, curvilinear, spherical and the like. The substrate 16 may be formed from a wide variety of materials, and in various embodiments, which are not intended to be limiting, can be glass, a polymeric film, a metal, a surface of an electronic component such as, for example, a silicon wafer, a fabric, human or animal skin, and the like.

In FIG. 1A-1, the surface 14 of the substrate 16 occupies the x-y plane, and the filaments 12 are applied in a toolpath pattern 20 on the surface 14. In the embodiment of FIG. 1A-1, the toolpath 20 when viewed from a perspective above the x-y plane of the surface 14 includes an arrangement of substantially linear filaments 12, but the toolpath pattern 20 may include circular patterns, arcuate patterns, trapezoidal patterns, and combinations thereof. For example, in FIGS. 1A-2 and 1A-3 the filaments 12 are arranged in substantially linear toolpath patterns when viewed above the x-y plane, while in FIGS. 1A-4 the filaments 12 are arranged in a trapezoidal toolpath pattern 20, and FIG. 1A-5 the filaments 12 are arranged in a substantially circular toolpath pattern 20.

Referring again to FIG. 1A-1, to form the 3D printed structure 10, the filaments 12 are stacked on each other along their longest dimensions (lengths) such that adjacent filaments overlie and adhere to one another to form a wall-like structure 30. As shown in FIG. 1A-1, the filaments 12 may be stacked in adjacent parallel planes normal to the x-y plane (the z-x plane and the y-z plane) to form the enclosed structure 10, which includes an internal passage 32.

As shown in FIG. 1B-1, a cross-section of an embodiment of a wall structure 30 as viewed in a plane normal to the plane of the surface 14 of the substrate 16 (for example, the y-z plane normal to the x-y plane in FIG. 1A-1) includes a first elongate filament $12_0$ on the surface 14 of the substrate 16. To form the wall 30, a series of filaments $12_1$-$12_n$ are formed on the first elongate filament $12_0$. The nozzle 4 moves along an angle in the plane normal to the x-y plane and extrudes each filament $12_1$-$12_n$ formed in a plane substantially parallel to the x-y plane of the first filament $12_0$. The filaments $12_0$-$12_n$ adhere to each other along their lengths to form the wall structure 30. While the example filaments $12_0$-$12_n$ in FIG. 1B-1 are shown with a substantially circular cross-sectional shape, depending on the polymeric materials selected to form the filaments 12 and a cross-sectional shape of the extrusion nozzle 4 (FIG. 1A-1), many different cross-sectional shapes are possible, including regular shapes such as squares, trapezoids, ovals and the like, as well as irregular shapes. In various embodiments, which are not intended to be limiting, the filaments 12 have a cross-sectional diameter of about 100 nm to about 500 µm, or about 100 nm to about 200 µm, or about 100 nm to about 100 µm.

The composition utilized to make the filaments 12, which can also be referred to as an ink, can vary widely depending on the intended use of the printed structure 10. Suitable ink materials should include at least one polymeric material with suitable yield strength, elastomeric properties, and good adhesion to surfaces. In various embodiments, which are not intended to be limiting, the polymeric materials can include silicones, (meth)acrylates (wherein (meth)acrylate includes acrylates and methacrylates) such as polymethylmethacrylate (PMMA), polystyrene, poly(ethylene glycol) diacrylate (PEGDA), polymeric materials and gels available from Lubrizol Life Science, Bethlehem, Pa. under the trade designation CARBOPOL, hydrogels, and biodegradable polymers such as polylacticcoglycolic acid (PLGA), biocompatible polymers available from Eden Microfluidics, Paris, FR, under the trade designation FLEXDYM, and thiolenes.

In some examples, the ink includes a silicone compound, which may be hardenable at room temperature, with heat, or with radiation such as, for example, UV light. In some embodiments, the silicone utilized to make the filaments 12 is an acetoxy silicone that is room temperature vulcanizing (RTV) when exposed to moisture in the air.

In one example, which is not intended to be limiting, a suitable silicone compound for the ink is a one-part acetoxy silicone available under the trade designation LOCTITE SI 595 CL from Henkel, AG, Minneapolis, Minn. This one-part silicone does not require prior mixing or other preparation and cures in ambient environment without requiring UV irradiation or thermal heating. In addition, cured RTV silicone structures made from acetoxy silicones demonstrate high elongation before breaking and good adhesion to different surfaces. In some embodiments, which are not intended to be limiting, the acetoxy silicone has a Young's modulus of about 10 kPa to 10 MPa, or 150 kPa to about 250 kPa, or about 175 kPa to about 200 kPa, or about 190 kPa.

Referring to the schematic diagram in FIG. 1B-3 and the associated plots in FIGS. 1B-4 to 1B-7, the behavior of the printed walls 30 can be analyzed using a cantilever beam model with evenly distributed gravitational loading to analyze the distribution of the bending moment along the silicone walls.

$$M_x = \frac{\gamma}{2\cos(\alpha)} x^2 \quad (1)$$

$$M = \frac{1}{2} \gamma l^2 \cos(\alpha) \quad (2)$$

Where $M_x$ is the bending moment of a cross-section at location x, y is the linear specific weight of the silicone wall, α is the wall incline angle, M is the maximum bending moment at the root of the wall and l is the total length of the wall. This model indicates that the magnitude of the bending moment increases parabolically in the direction towards the substrate, making the root of the wall the weakest point. For a fixed length of the wall, the maximum bending moment increases as the incline angle decreases. In various example embodiments, which are not intended to be limiting, a self-supporting wall 30 has a length l of about 10 µm to about 10 mm, or less than about 1 mm, or less than about 700 µm, or less than 500 µm. In various example embodiments, the self-supporting wall 30 should have a thickness t of less than about 500 µm, or less than about 300 µm, or less than about 200 µm.

In some embodiments, the ink can include optional fillers to modify its properties such as, for example, nano or microparticles such as $Al_2O_3$ or $SiO_2$ to provide reinforcement, or metal particles such as Ag, Au, carbon black, graphene, and the like to enhance electrical conductivity.

In some examples, the inks can include a wide variety of non-polar solvents such as, for example, hexane, to dilute the ink, or photo-initiators such as benzophenone and isopropyl thioxanthone to accelerate the UV curing process.

In some examples, the printed structure 10 of FIG. 1A-1 can include optional sacrificial materials, which can be used to temporarily support the structure 10 during, for example, printing and curing steps. For example, the sacrificial materials can be printed with a second ink different from the first polymeric ink, and can be used to temporarily fill hollow channels and chambers. The sacrificial materials are then removed from the printed structure during or after the curing or hardening process. Suitable sacrificial materials include, but are not limited to, pluronics (block copolymers including hydrophilic polyethyleneoxide (PEO) and hydrophobic polypropylene oxide (PPO) blocks), sugar networks, water soluble polymers, acrylonitrile butadiene styrene (ABS), paraffin-based inks such as, for example, Prussian blue paste, petroleum jelly, microcrystalline wax, carbohydrate gels, hydrogels, liquid metals, and mixtures and combinations thereof.

As shown in FIGS. 1B-1 and 1B-3, when viewed in a plane normal to the plane of the surface 14 to which filament $12_0$ is applied (for example, the y-z plane normal to the x-y plane in FIG. 1A-1), the wall 30 forms a wall angle α with respect to the plane of the surface 14. For as-printed walls 30 in the sub-millimeter regime, the yield strength of the as-printed silicone-containing ink is sufficient to balance the bending moment induced by gravity within a predetermined angular range. As shown in the examples in FIGS. 1B(a) and 1B(b), in various embodiments the wall angle α can vary widely from about 35° to about 90°, or about 37° to about 90°, or about 45° to about 90°, or about 37° to about 75°, or about 45° to about 60°.

As shown schematically in FIGS. 1B-1, 1B-2, and 1B-3, the wall 30 formed from the silicone-containing ink composition has a maximum bending moment M proportional to cos(α), and if the wall has a length of about 700 μm and wall angle α greater than about 35°, the wall 30 will effectively resist gravitational loading exerted in a direction normal to the surface 14 and form a self-supporting wall structure (See, for example, FIGS. 1B(a) and 1B(b)). However, if the wall angle α drops below about 35°, depending on factors such as, for example, the polymeric material used to form the filaments 12, and the cross-sectional dimensions of the filaments 12, in some cases the wall 30 cannot support its own weight, and the gravitational loading causes the wall to collapse (FIG. 1B(c)).

While not wishing to be bound by any theory, presently available evidence indicates that an uncured RTV (room temperature vulcanizing) silicone such as LOCTITE SI 595 CL exhibits the mechanical behavior of a yield-stress fluid, with storage modulus greater than loss modulus at low frequency. This renders a yield stress that must be overcome to initiate flow under the gravitational loading. Because the RTV silicone starts curing instantaneously after dispensing, as evidenced by increasing storage modulus over time, the predicted yield strength is slightly higher than the measured value. RTV silicone also exhibits shear thinning behavior in the uncured state. Briefly, in some example embodiments, which are not intended to be limiting, RTV silicones such as LOCTITE SI 595 CL have an apparent viscosity of about 104 Pa·s at a shear rate of 0.01 s$^{-1}$, and the viscosity decreases to about 10$^{-3}$ Pa·s as the shear rate increases to 1000 s$^{-1}$. This variation in viscosity leads to a relatively low dispensing pressure through the nozzle 4 of about 175 psi with 100 μm printing nozzles, and a stronger resistance to creep for the as-printed structures.

Figures 1, 1B, 2:
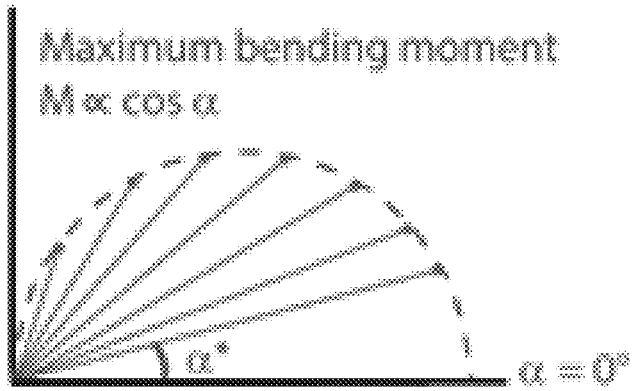
Figure 1B:
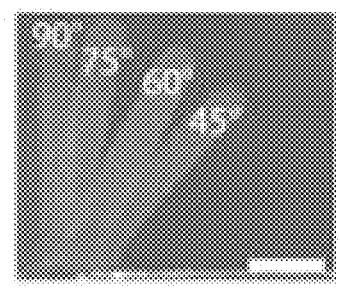
Figure 1B:
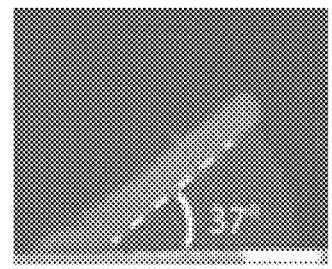
Figure 1B:
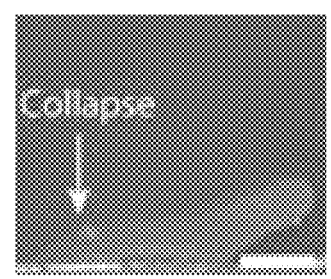
Figures 1, 1C:
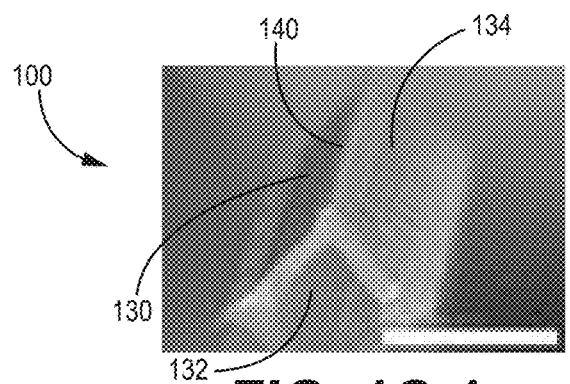
Figures 1, 1C, 2:
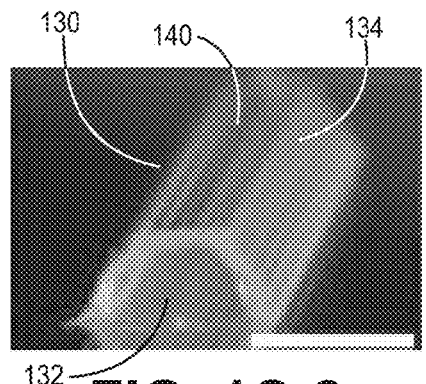

With the mechanical equilibrium states above the critical angle α, as shown in FIGS. 1C-1-1C-4, enclosed structures 100 could be formed from opposed silicone walls 130, 134 that are configured to meet in a roof-like apex region 140. As shown in FIG. 1C-1, in some examples the apex region 140 is a narrow seam formed from a single filament or a small number of filaments, and in other examples shown in FIG. 1C-2 the apex region 140 is a relatively wide, flat, planar portion of the structure 100 that itself is formed from multiple filaments. In other examples, the apex region 140 can be point or a narrowing frustoconical region atop the opposed walls 130, 134 (FIGS. 1C-3 and 1C-4). The enclosed structures 100 each include a continuous fluid passage 132, which can have a wide variety of cross-sectional shapes including triangular (FIG. 1C-1), trapezoidal (FIG. 1C-2), pyramidal (FIG. 1C-3), conical (FIG. 1C-4), square, and the like.

The geometries of the enclosed fluid passages 132 are based on the toolpaths in the X-Y plane and the vertical stacking angle of the filaments used to form the opposed walls 130, 134 (FIGS. 1A-1, 1A-2, 1A-3). The dimensions of the fluid passages 132 can be selected by specifying the distance between the opposed sidewalls 130, 134 sidewalls and the incline angle α. The printing toolpath 20 (FIG. 1A-1) is determined based on, for example, the thicknesses of the extruded filaments 12, calibrated with the size of the printing nozzle 4 and the extrusion pressure of the polymeric material. In various embodiments, which are not intended to be limiting, the fluid passages 132 have an inner cross-sectional width w of about 100 μm to about 500 μm (FIGS. 1D-1, 1D-2).

In some cases, each of the walls 130, 134 may include the same number of filaments, but in other examples one or both walls may be designed to include an extra filament or group of filaments referred to herein as a spacer filament. The number, location, and size of the spacer filaments may be selected to modify the shape of the wall, the shape of the internal passage 32 between the opposed walls, or both. The spacer filaments can be formed from the same polymeric materials as the other filaments forming the walls 130, 134, or may be formed from a different polymeric material.

In some examples, overlying adjacent filaments 12 used to form the walls 130, 134 adhere to each other along their lengths to form a fluid-impermeable structure. If the opposed walls 130, 134 and the apex region 140 are fluid-impermeable, the enclosed fluid passages 132 within the structures 100 form self-supporting microfluidic devices. In various embodiments, the microfluidic structures 100 made from silicone-containing inks have a burst pressure of about 20 kPa to about 80 kPa, or about 20 kPa to about 50 kPa, or greater than about 40 kPa, at wall thicknesses of about 100 μm to about 400 μm (FIG. 1E). For example, at a wall thickness of about 200 μm, burst pressures fall in the range of about 30 kPa to about 50 kPa. For comparison, the backpressure applied to actuate aqueous flows in most microfluidic applications rarely exceeds about 10 kPa. While not wishing to be bound by any theory, computational fluid dynamic (CFD) simulations indicate that the microfluidic structures 100 required back pressures below 1 kPa, and the devices can be used repeatedly with no observable leakage at backpressures at a pressure of 10 kPa to about 75 kPa.

Microfluidic mixers can be used to rapidly and effectively mix chemical species in the typical low Reynolds number flow of microfluidic applications. In another embodiment, the extrusion-based printing procedures of the present disclosure can be used to produce complex channel arrangements and allow for the convenient incorporation of multiple materials within the same structure. By precisely designing printing toolpaths, multifunctional microfluidic constituents including, for example, channel-chamber transitions, T-shaped intersections and overlapping channels can be printed with the self-supporting structures.

Referring now to an example shown FIG. 2, a microfluidic mixing device 200 3D printed on a surface 214 of a substrate 216 includes an arrangement 250 of structures 252. The structures 252 extend away from the surface 214, and may have any suitable shape. In the non-limiting example embodiment of FIG. 2, the structures form angled ridges. The ridges 252 each include a long portion 254 and a short portion 256. As shown schematically in the depiction of the embodiment of FIG. 2, the ridges 252 each have a thickness of about 150 µm, long portions 254 with a length of about 550 µm, and short portions 256 with a length of about 400 µm.

A body portion 260 is printed to at least partially bound the arrangement 250 of the ridges 252. The body portion 260 includes opposing walls 230, 234, which have an elongate, substantially linear shape when viewed above a plane of the surface 214. Each of the first wall 230 and the second wall 234 have a wall angle of about 35° to about 90° with respect to a plane of the surface 214. The opposed walls 230, 234, which are each self-supporting and liquid impermeable, extend away from the surface 214 and are joined by an apex region to form an enclosed passage 232 with a trapezoidal cross-sectional shape.

In the embodiment of FIG. 2, the ridges 252 are arranged in a regular pattern 250 with a first portion oriented to have the long side 256 proximal the wall 230 of the body portion 260, and the short side proximal the wall 234 of the body portion 260. A second portion of the pattern 250 of the ridges 252 are oriented to have the long side proximal the wall 234, and the short side proximal the wall 230. The pattern 250 thus has a herringbone-like appearance, which in various embodiments can be regular or irregular and can include any number or orientation of the angled ridges 252.

The mixing device 200 further includes a T-shaped inlet portion 270 with a first inlet 272 and a second inlet 274, which are fluidly connected to a feed passage 266. The feed passage 266 is in turn fluidly connected to an inlet 261 of the body 260. An outlet 263 of the body 260 is fluidly connected to an outlet portion 278.

The mixing device 200 thus includes a continuous internal microfluidic passage wherein a first fluid 280 is supplied to the first inlet 272, and a second fluid 282 different from the first fluid 280 is applied to the second inlet 274. The first fluid 280 and the second fluid 282 then enter the feed passage 266, and subsequently enter the fluid passage 232 in the body portion 260 of the device 200. As the fluids 280, 282 traverse the alternating herringbone ridges 252, turbulence and fluid mixing occur, and a substantially uniformly mixed fluid 284 emerges from the outlet 278 of the device 200.

In some embodiments, the walls 230, 234 of the device 200 may be printed from a first polymeric material, and the other structures such as ridges 252 may be printed from a second polymeric material different from the first polymeric material. In one example embodiment, which is not intended to be limiting, the walls 230, 234 are formed from a silicone material such the RTV silicone described above, and the ridges 252 are formed from a more rigid material such as a polycaprolactone (PCL).

As discussed in more detail in the examples below, the device 200 of FIG. 2 may be 3D printed by initially extruding the arrangement 250 of the ridges 252 on the surface 214 of the surface 216, or by using a preformed substrate with cast ridges or other structures. An elongate base filament is then printed to form a base for the walls 230, 234 of the body portion 260, which at least partially bound the arrangement 250 of the ridges 252. The elongate base filament further includes the T-shaped inlet portion 270 and the outlet portion 278. Additional filaments are then stacked on the base to form the liquid impermeable walls 230, 234, and the remainder of the walls of the inlet portion 270 and the outlet portion 278. Next, a roof-like apex portion 240 is formed to enclose the inlet portion 270, the body portion 260, and the outlet portion 278 to create an enclosed microfluidic passage that fluidically connects the inlet portion 270, the body portion 260, and the outlet portion 278.

There has been a persistent effort to integrate microfluidics with electronic sensors to create high-throughput sensing platforms. Such systems can suffer from either the time-consuming process involved with soft lithography, stamp distortions, misalignment issues and resulting surface contamination, or a bulky encapsulation for the microfluidic components. In another embodiment, the self-supporting microfluidic structures fabricated with extrusion-based 3D printing process of the present disclosure provide a solution to seamlessly merge microfluidic devices and electronics. For example, a microfluidic structure can be directly printed on a sensor array, realizing synchronous alignment and integration during the printing process. For example, in some embodiments, the microfluidic structure and the sensor array can be aligned with a precision of at least about 100 nm, or about 50 nm, or about 25 nm.

Figures 1, 1C, 2, 3:
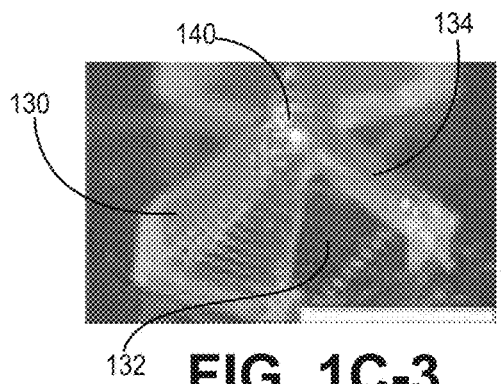
Figures 1, 1C, 2, 3, 4:
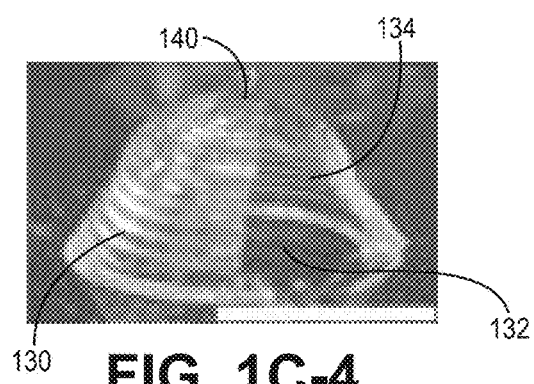
Figures 1, 1D:
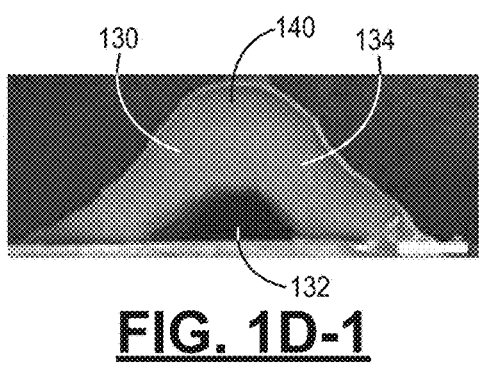
Figures 1, 1D, 2:
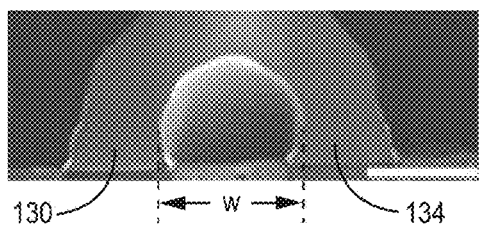
Figure 1E:
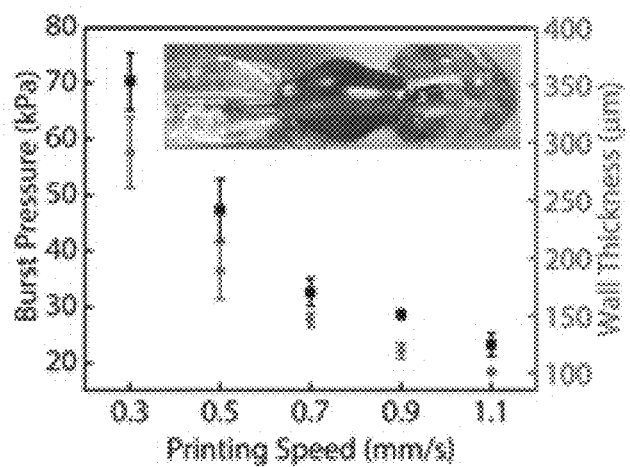
FIG. 1E is a plot of burst pressure and wall thickness of triangular channels with respect to printing speed. The inset photo shows one specimen under test with a length of 5 mm and a wall thickness of about 150 μm.

Referring now to the schematic illustration in FIG. 3, an array 302 of sensing electrodes 304A-D and alignment marks 306 were pre-deposited on a surface 308 of a substrate of an electronic device 310 such as, for example, a silicon wafer. Prior to printing, the alignment marks 306 were used to position the array of sensing electrodes 302 in a predetermined location within the coordinate system of the 3D printer. Any suitable electrode may be used including, but not limited to, resistance based 2-point electrodes, FET electrodes, and the like.

A polymeric ink was then extruded in overlying elongate filaments on the surface 308 of the electronic device 310 to construct an arrangement of self-supporting microfluidic structures with liquid impermeable walls. A microfluidic device 300 was printed on the surface 308 of the electronic device 310 to provide fluid flow over the sensing electrodes 304A-D. The microfluidic device 300 includes an inlet passage 320 fluidically connected to a first chamber 322 overlying the sensing electrode 304A. A connecting channel 330 fluidically connects the first chamber 322 to a second chamber 324 overlying the second electrode 304B. A connecting channel 332 fluidically connects the second chamber 324 to a third chamber 326 overlying the sensing electrode 304C. The third chamber is fluidically connected to a fourth chamber 328 via a connecting channel 334. The fourth chamber 328 is fluidically connected to an outlet 340.

The serially connected microfluidic channels and chambers printed on top of the sensor array 302 provide a fluid flow over any, all, or a selected number of the sensors 304A-D. For example, in some embodiments, by activating selected printed valves, the fluid flow can be directed in a pre-determined and changeable order over one or any combination of the connected sensors 304A-D. A robust adhesion is formed between the substrate surface 308 and the 3D printed parts of the device 300 to create a compact form-factor that can be used to guide the flow of an analyte solution over the sensors 304A-D. For example, impedance measurements can be used to determine properties of the analyte solution as it interacts with the sensor array 302.

In various embodiments, the 3D-printed device 300 can be utilized as a part of any type of chemical sensing array such as, for example, a salinity sensor, or as part of a high-throughput biochemical diagnostic assay through the integration of sensing arrays that are functionalized with probing molecules including DNA, RNA, aptamers, peptides, proteins and antibodies. For example, each sensor 304 of the electronic device 310 can be functionalized via 3D printing to create diverse sensing arrays for the multiplexed detection of various targets within one microfluidic chip.

With the extrusion-based 3D printing method of the present disclosure, in another embodiment self-supporting microfluidic structures can be used to create functional microfluidic valves and pumps that are conformal to planar or non-planar surfaces via overlapping silicone channels and encapsulation.

Figure 4A:
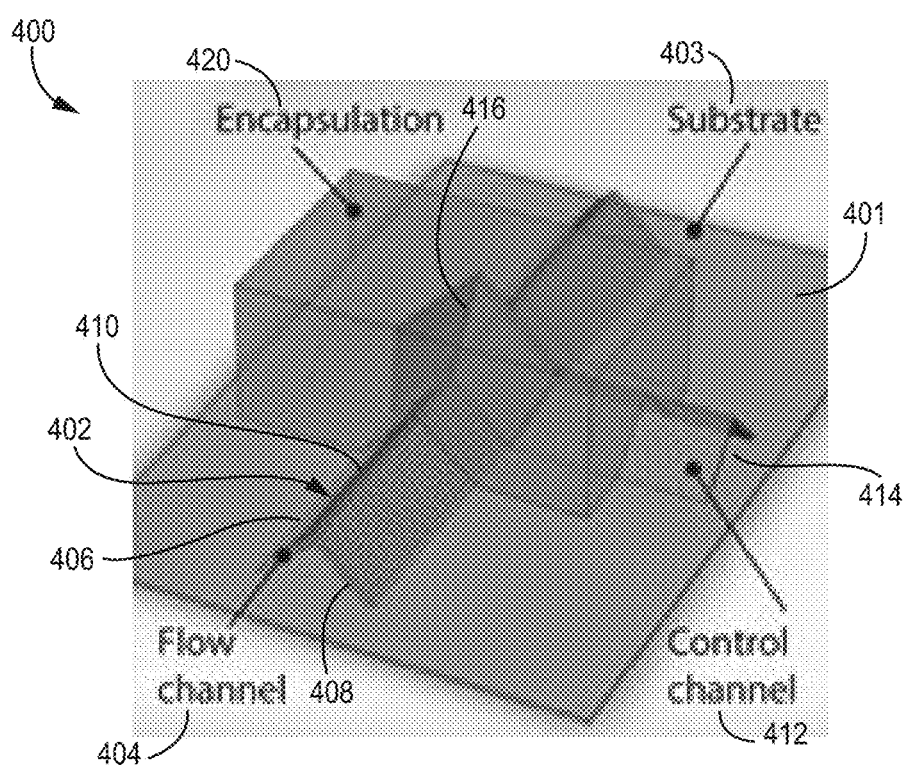
FIG. 4A is a schematic representation of an embodiment of a 3D printed microfluidic valve construction.

Referring now to FIG. 4A, a 3D printed microfluidic valve 400 includes an elongate structure 402 extruded on a surface 401 of a substrate 403. The structure 402 is formed with a plurality of polymeric filaments stacked on each other along their lengths as described in FIG. 1A-1 above, and the filaments enclose a flow channel 404 for transporting a liquid or a gaseous material. The structure 402 includes opposed liquid impermeable walls 406, 408 that merge in an apex region 410, each of the walls 406, 408 having a wall angle of greater than about 35°. In some embodiments, which are not intended to be limiting, the polymeric filaments used to make the structure 402 are formed from the RTV silicone materials described above.

A control channel 412 is conformally printed over a portion of the structure 402. The control channel 412, which was also 3D printed using stacked polymeric filaments as described above, also includes an enclosed fluid passage 414. In some embodiments, which are not intended to be limiting, the polymeric filaments used to make the flow channel 402 are formed from the RTV silicone materials described above. The control channel 412 further includes a valve section 416 that overlies the flow channel 404 at a crossing junction therewith. An enclosed hollow space is formed between the two channels 404, 412 to act as a valve when actuated by pressurized gas flowing through the fluid passage 414.

The valve section 416 is overlain and encapsulated by an encapsulant structure 420. The encapsulant structure can be formed from any suitable encapsulant material, and acrylate ester-based resins have been found to particularly suitable. In some cases, the acrylate ester resins can be curable by radiation such as UV light. Given the presence of the overlying encapsulant structure 420, downward expansion of a pressurized gas in the control channel 412 acts on the flow channel 402 and closes the valve section 416. The highly elastic walls of the control channel 412 and the flow channel 402 thus form a flexible native membrane to open or close the valve section 416.

In some embodiments, the control channel 412 can be interfaced with external tubes (not shown in FIG. 4A) and sealed directly with the encapsulation resin. Generally, a higher flow pressure in the flow channel 402 requires a correspondingly higher closing pressure in the control channel 412 to stop the flow. For example, in some embodiments, a 300 kPa controlling pressure in the control channel 412 closed the valve 416 completely while a hydraulic pressure up to 30 kPa was applied to the flow channel 402.

In another embodiment, peristaltic microfluidic pumps can also be directly 3D printed using three controlling channels laid out in parallel and encapsulated as one unit. The microfluidic pump was operated by activating the control channels according a three-phase peristaltic code. Longer actuation times yielded a more complete shut-off of the control channels and therefore could be tuned to generate a higher pumping volume per cycle. In one example embodiment, a flow rate of 105 L/cycle was achieved with an actuation pressure of 100 kPa and an actuation time of 1.2 sec.

Figure 4B:
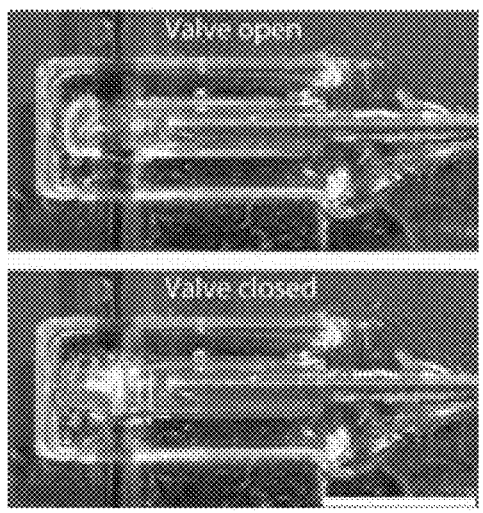
FIG. 4B includes photographs displaying the open and closed states of the 3D printed microfluidic valve of Example 4, with a scale bar of 3 mm. The valve was closed with a pressure of 100 kPa.

In another example, microfluidics-based biomedical applications such as physiological status monitoring via sweat collection and sensing require the direct conformal integration of microfluidic networks onto curvilinear surfaces such as human skin. As shown in the examples below, the flexibility and stretchability of the 3D printed self-supporting structures made according to the techniques of the present disclosure make possible the directing printing of self-supporting microfluidic structures onto a wide variety of 3D targets including non-planar substrates. For example, FIGS. 4E-4F in the examples below show self-supporting microfluidic structures can be 3D printed on a spherical surface such as a spherical 10 ml flask.

In some embodiments, which are not intended to be limiting and are provided as an example, the self-supporting microfluidic structures can be wrapped around a glass rod with a radius as small as 2.5 mm without damage, were found be stretchable in a flow direction by about 40% to about 100%, and were stretchable in a transverse direction by about 85%.

In one example, the self-supporting microfluidic structures could be printed on freeform surfaces such as, for example, human skin, to form any type of physiological sensor and to wick sweat or other bodily fluids from the skin into the microchannels.

Figure 5:
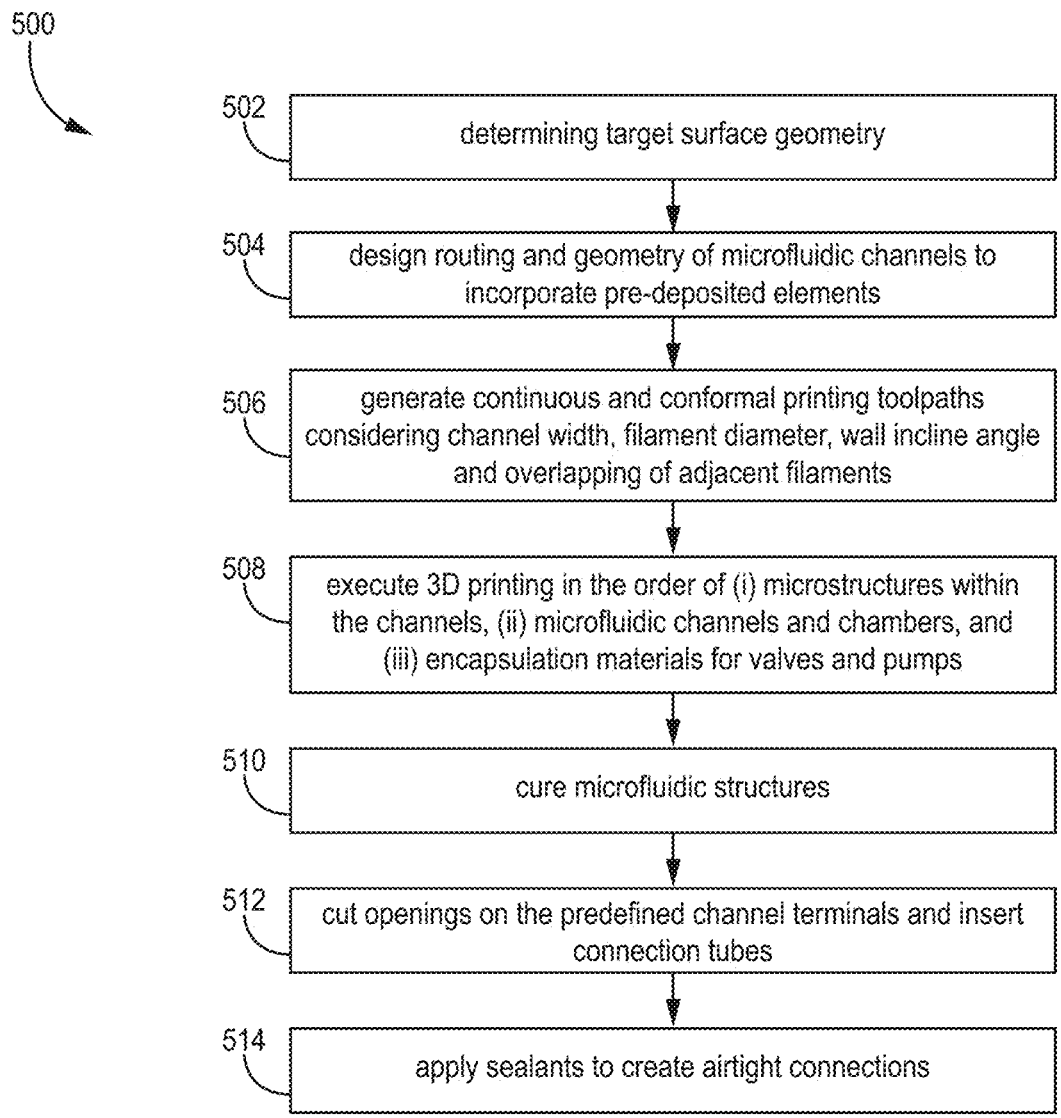

Referring now to FIG. 5, the present disclosure is further directed to a method 500 for 3D printing a microfluidic device on a substrate. In step 502, the method includes mathematically reconstructing the target surface geometry. In step 504, the method further includes designing and routing and geometry of microfluidic channels to incorporate pre-deposited elements. In step 506, the method further includes generating continuous and conformal printing toolpaths considering parameters such as, for example, channel width, filament diameter, wall incline angle and overlapping of adjacent filaments. In step 508, the method further includes executing 3D printing in the order of: (i) microstructures within the channels, (ii) microfluidic channels and chambers, and (iii) encapsulation materials for valves and pumps. In step 510, the method further includes curing the microfluidic structures. In optional step 512, the method further includes cutting openings on the predefined channel terminals and insertion of connection tubes. In optional step 514, the method includes applying sealants to create airtight connections. The excellent elasticity of the cured silicone channels enables a facile and tight connection to external tubing.

Embodiments of the systems, devices and methods of the present disclosure will now be further described in the following non-limiting examples.

EXAMPLES

Example 1

Methods for Printing Self-Supporting Microfluidic Structures

To make the 3D printed structures shown in FIGS. 1A-1E described above, the diameters of extruded silicone filaments were characterized with a microscope (available under the trade designation Leica DM4500 from Leica Camera AG, Wetzlar, Del.) and correlated to printing parameters including the inner diameter of the printing nozzles (available from Nordson EFD, Providence, R.I.), dispensing pressure (available under the trade designation Ultimus V Dispenser, Nordson EFD) and translational speed. The silicone compound used to make the filaments was a one-part acetoxy silicone available under the trade designation LOC-TITE SI 595 CL from Henkel, AG, Minneapolis, Minn.

Next, the stacking orientation and spacing between adjacent filaments was calculated to ensure a 30-50% overlap. After the microfluidic routes and geometry of the substrate were determined, two dimensional (2D) continuous toolpaths of the printing nozzle were designed with the software CADFusion (Aerotech Inc., Pittsburgh, Pa.). To generate the printing toolpaths for the spherical microfluidics, the cross-sections of channels with different distances to the sphere center were inspected, and 'spacer' layers were added to ensure even spacing between adjacent filaments. A MATLAB script was then used to divide the 2D toolpaths into 50 mm (20 mm for valves) straight elements, and the Z coordinates were calculated based on the radii of the corresponding layers. The calculated coordinates were written into G-code and outputted from the MATLAB script.

To clean the target surfaces, polyethylene terephthalate (PET) films and spherical glass flasks were sonicated in acetone, isopropanol and DI water sequentially for 5 min each and blown dry with high-purity nitrogen (99.998%).

Then the uncured silicone ink was extruded on a robotic gantry system (available under the trade designation AGS1000 from Aerotech, Inc.) to print the microfluidic structures on the target surfaces. The printing conditions used to form the polymeric filaments used in the Examples are shown in Table 1 below.

TABLE 1

| Device Type | Nozzle Type | Nozzle Inner Diameter (µm) | Pressure (psi) | Speed (mm/s) | Distance to Substrate (µm) | Toolpath Resolution (µm) | Interlayer Distance (µm) |
|---|---|---|---|---|---|---|---|
| Planar | Stainless steel | 100 | 175 | 5 | 100 | Continuous | 70 |
| Spherical | Tapered polypropylene | 200 | 25 | 3 | 200 | 20 (valves) 50 (channels) | 120 |

The printed structures were fully vulcanized in air for 5 hours before testing. Metal tubes (23-25 gauge, Nordson EFD) were inserted into the 3D printed silicone channels and sealed with epoxy to connect with external liquid sources.

Example 2

Microfluidic Mixer

To demonstrate the high geometric modeling accuracy of the systems and methods of the present disclosure, 3D printed microfluidic mixers similar to those described above in FIG. 2 were made as described in Example 1 above. The printed structures included self-supporting silicone channels and embedded polycaprolactone (PCL) herringbone (HB) ridges.

Figure 2:
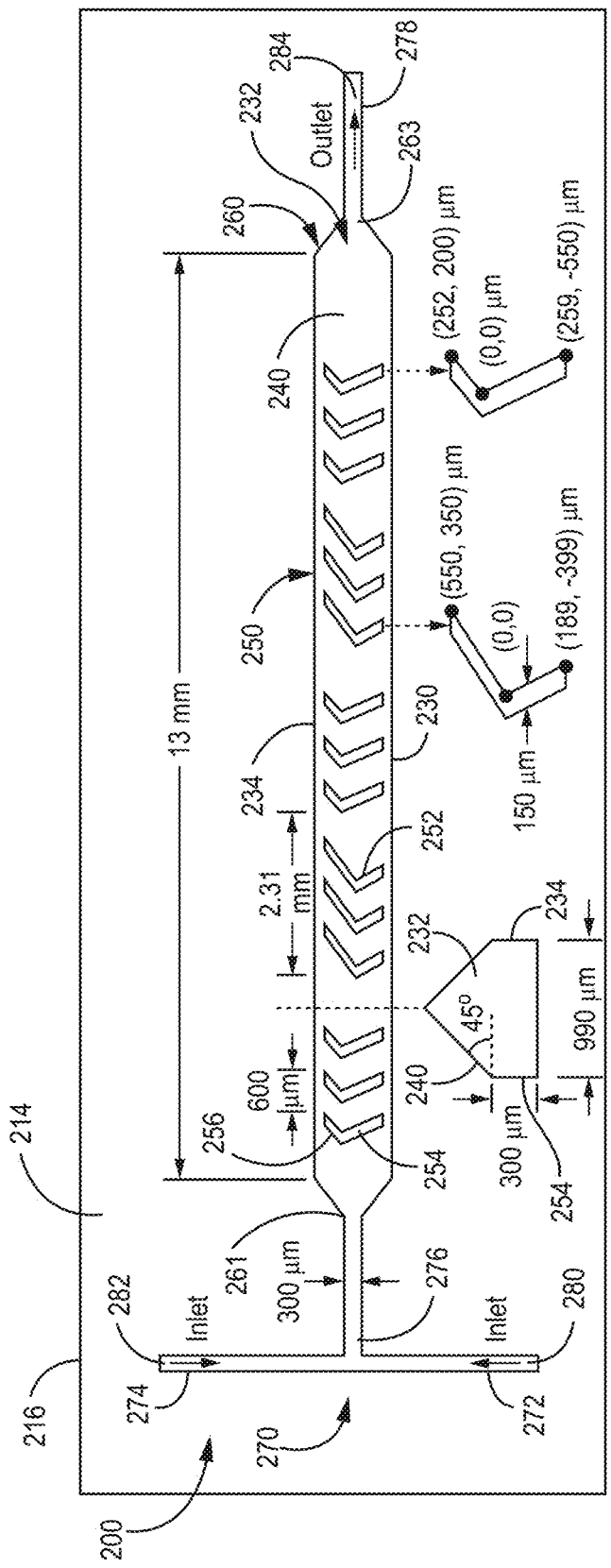
Figure 2A:
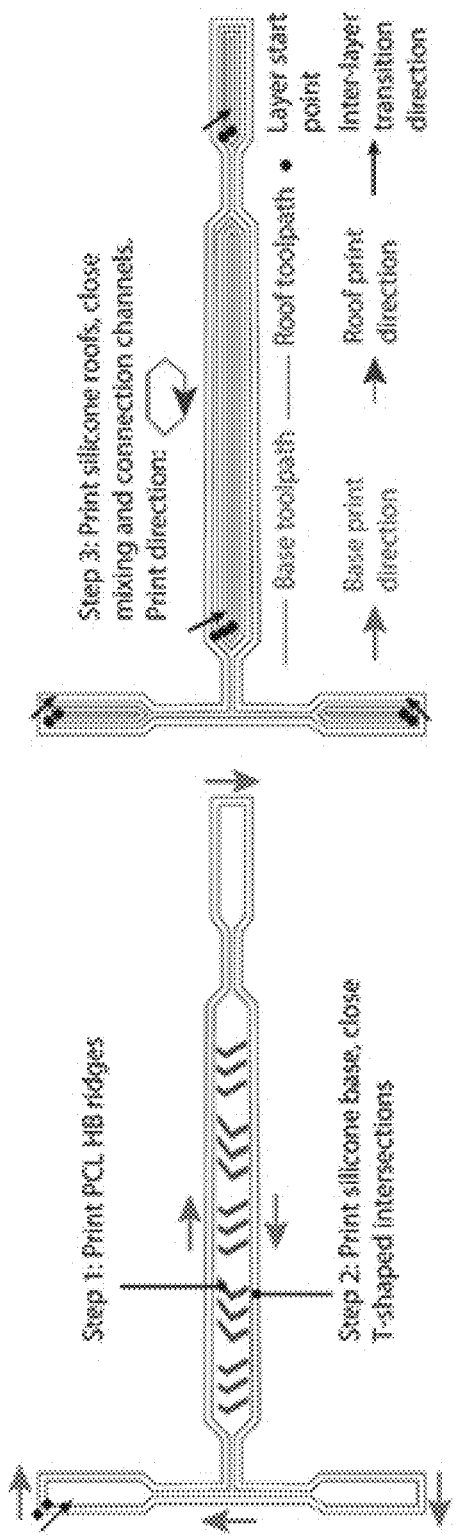
FIG. 2A is schematic representation of a three-step printing procedure to make the mixer of FIG. 2. Continuous toolpaths were designed to minimize disruption in ink extrusion and realize leakage-free connections between channels.

Referring now to FIG. 2A, the mixers consisted of a T-shaped inlet intersection and a main mixing channel where the herringbone ridges were housed. Five sets of HB ridges with variable heights were embedded within the 990 µm wide mixing channels. Three steps were adopted to print the mixers (FIG. 2A). First, the HB ridges were printed on the polyethylene terephthalate (PET) substrates with an inter-layer resolution of 30 For the microfluidic mixers, the HB ridges in the mixing channels were printed with polycaprolactone (PCL) (PCL 440744, obtained from Sigma-Aldrich), dissolved in dichloromethane at a concentration of 20 wt. %, and printed with a pressure of 35 psi and speed of 0.2 mm/s. The inter-layer resolution of HB ridges was 30 and the printing nozzles had an inner diameter of 80 µm (available under the trade designation TE734025PK from Techcon, Inc., Cypress, Calif.).

Figure 2C:
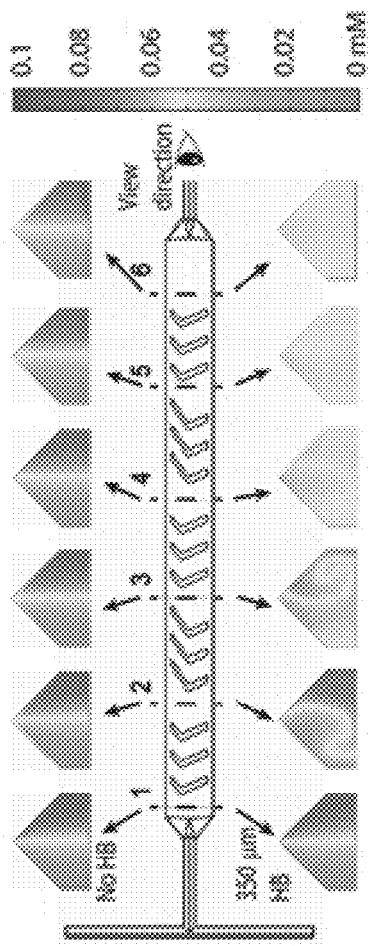
FIG. 2C is a computational fluid dynamics (CFD) simulation of chemical species mixing at 6 cross-sections of the microfluidic mixer of Example 2 with Re=1. The mixing evolution along the mixing channel without and with HB ridges (350 μm) are displayed in the upper and lower panel, respectively.
Figure 2B:
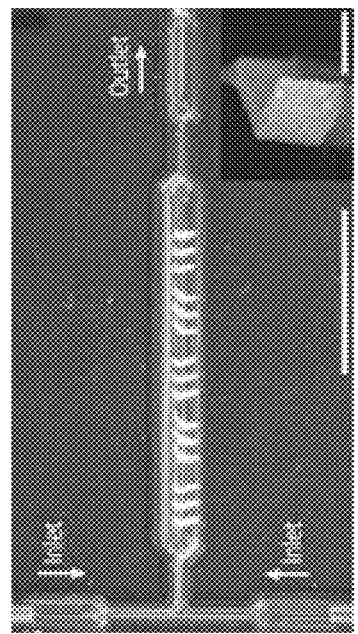
FIG. 2B is an overhead view of the 3D printed mixer made according to Example 2, with a scale bar of 5 mm. The inset photo, which has a scale bar of 300 μm, shows one herringbone (HB) ridge printed with polycaprolactone (PCL).

Then, to print the base, i.e., the lower channels including the T-shaped intersections, continuous and cycling printing toolpaths were executed to eliminate the disruption to the ink dispensing. Finally, after the lower channels were closed, the nozzle was lifted and translated to the next higher channel that remained open, and another continuous toolpath was executed to close the roof. The specifically designed continuous toolpaths prevented discrepancies in filament connection, creating leakage-free channel intersections and transitions between differently sized channels. FIG. 2B illustrates the 3D printed mixer that was embedded with 350 µm tall HB ridges.

The two inlets were each inputted with solutions of dextran (ca. 10 kDa) that were modified with rhodamine B (red) (dextran-RB, R8881, Sigma-Aldrich) or fluorescein isothiocyanate (green), (dextran-fluorescein isothiocyanate (dextran-FITC, FD10S, Sigma-Aldrich)). The input solutions had an initial concentration of 0.1 mM. FIG. 2C compares the mixing effects of two mixers at Re=1, one without HB ridges (upper row) and one with 350 µm tall embedded HB ridges (lower row). An inspection of six selected cross-sections along the channels showed significant improvement in the extent of mixing, with the latter generating a well-mixed output.

Next, the performance of the mixers was validated with CFD simulation and confocal microscopic imaging. CFD models were built in the Stokes flow regime, where the Reynolds number is no greater than one (Re≤1). The CFD simulation was conducted with the finite element analysis software COMSOL Multiphysics (available from COMSOL, Inc., Burlington, Mass.). Two modules, Laminar Flow and Transport of Diluted Species, were coupled to simulate the chemical species mixing.

The laminar flow was simulated based on the continuity and Navier-Stokes equations:

$$\nabla \cdot (\rho u) = 0 \qquad (1)$$

$$\rho u \cdot \nabla u = -\nabla p + \nabla (\mu(\nabla u + (\nabla u)^T)) \qquad (2)$$

where u is the fluid velocity, p is the fluid pressure, ρ is the fluid density and μ is the fluid dynamic viscosity. The transport of diluted species was simulated based on the convection-diffusion equation:

$$\frac{\partial c_i}{\partial t} + \nabla \cdot (-D_i \nabla c_i + c_i u) = 0 \qquad (3)$$

where $c_i$ and $D_i$ are the concentration and diffusivity of species i, respectively.

Water at 25° C. was defined as the carrier fluid with a density of 1000 kg/m³ and a dynamic viscosity of 8.9×10⁻⁴ Pa·s. Boundary conditions include a rigid and non-slippery wall, uniform velocity at the two inlets for different Reynolds numbers, input concentration of 0.1 mM for the two species and a zero outlet pressure. Diffusivity of the fluorescent labeled dextran molecules was calculated based on the Stokes-Einstein equation:

$$D = \frac{k_B T}{6\pi \mu R_H} \qquad (4)$$

where D is the diffusivity of the investigated molecules, $k_B$ is Boltzmann constant, T is temperature and $R_H$ is the hydrodynamic radius of the molecules. With a molecular weight of ca. 10 kDa, the dextran molecules were estimated to have a hydrodynamic radius of 6 nm and a diffusivity of 4.02×10⁻¹¹ m²/s. For the meshing of the simulated geometry, an iterative increase in the number of nodes showed that 61,400 nodes are sufficient for the simulation. To evaluate the mixing indices according to Equation (3), the concentration information of species A was extracted from a cut plane with 6,900 points selected from an orthogonal grid on the plane.

The mixing effect was quantitatively evaluated with the mixing index W:

$$W = 1 - \frac{\sigma}{\sigma_{max}} \qquad (5)$$

where σ is the standard deviation of the concentration of one selected species within a cross-section and $\sigma_{max}$ is the standard deviation at the entrance of the mixing channel. Therefore, W is in the range of [0,1] and increases with the extent of mixing.

Figure 2D:
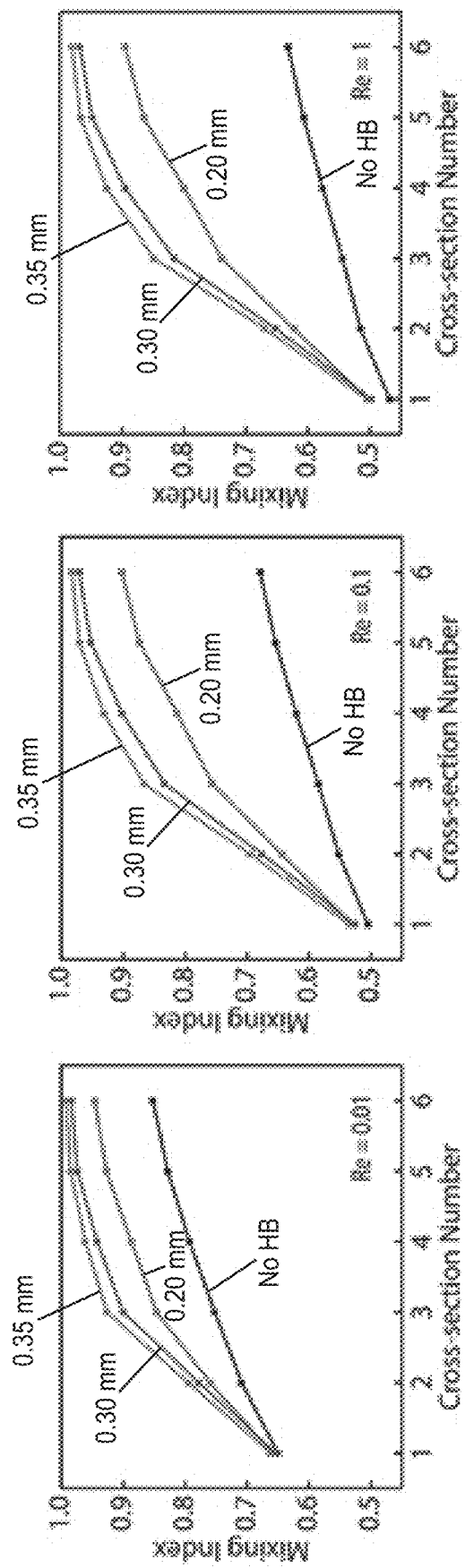
FIG. 2D includes plots of the simulated mixing indices with different heights of HB ridges within the Stokes flow regime (Re≤1) for the 3D printed microfluidic mixer of Example 2.

As expected, the mixing indices increased along the channel as the solutions flowed through the mixing channels even in the cases of no embedded HB ridges, as partial mixing was induced by molecular diffusion (FIG. 2D). This was also validated by the decreasing intensities of red and green colors from cross-sections 1 to 6 in the top row of FIG. 2C. The effect of diffusion was less significant for larger Re (higher flow rates), where diffusion occurred on a shorter timescale. Simulation showed that even at Re=1, the mixing index at the outlet approached the maximum with an HB ridge height of 350 μm. The significant enhancement of mixing was attributed to the local turbulence induced by the embedded PCL HB ridges.

To confirm that the CFD simulations represented the real mixing scenario, confocal microscopic images were acquired of the flow fields in the mixing channels. Images of the flow fields in the microfluidic channels were acquired on a laser-scanning confocal microscope (available under the trade designation Nikon A1Rsi, Nikon Instruments, Inc., Melville, N.Y.). The wavelengths of the lasers used to excite the red and green fluorescence were 561 nm and 488 nm, respectively.

The two molecules, dextran-RB and dextran-FITC, were dissolved in DI water at a concentration of 0.1 mM and injected into the mixers with a two-channel syringe pump (available under the trade designation Model Fusion 100CR, Chemyx, Inc., Stafford, Tex.). For each Reynolds number, images were taken after the flow reached a steady state with an exposure time of 2.1 s. The red and green channels were combined with ImageJ (1.52r, National Institutes of Health, USA), with which the quantitative intensity of the red channel was also measured.

Figure 2E:
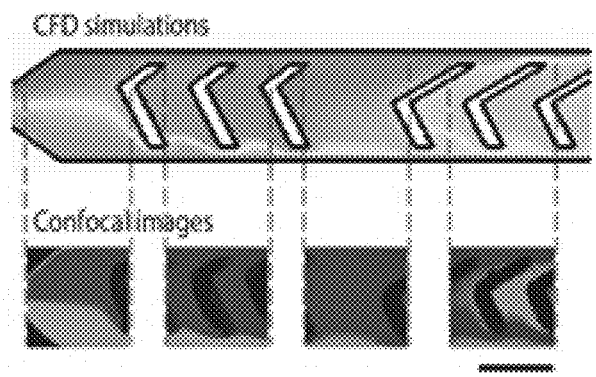
FIG. 2E is a comparison between the color maps of simulated concentration and confocal images at selected sections along the mixing channels. Imaging plane is 10 μm above the substrate. Re=1, HB height is 350 μm. Scale bar: 500 μm.
Figure 2F:
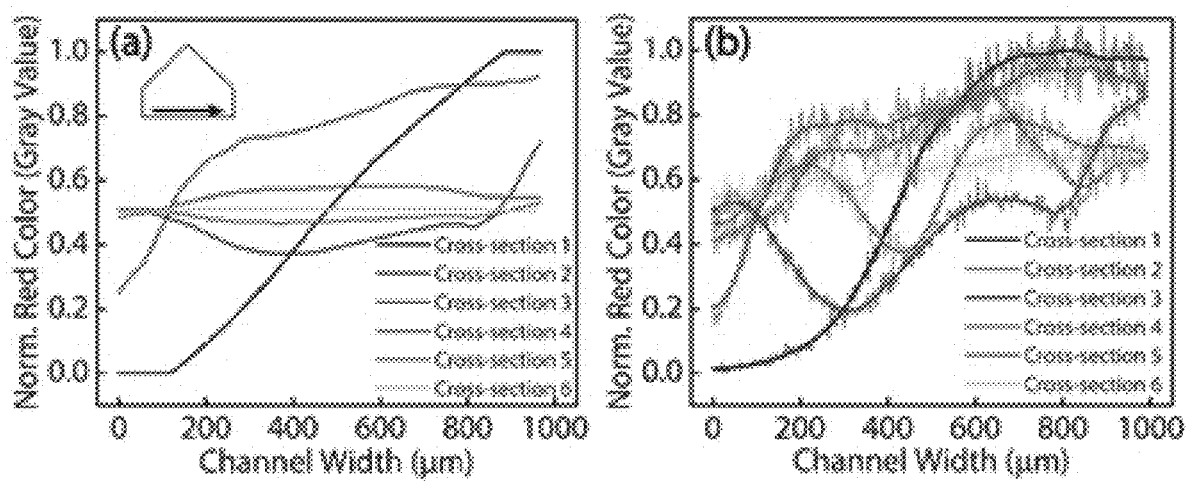
FIG. 2F includes two plots comparing red color intensity across the mixing channel at the above 6 cross-sections between (a) simulated color maps and (b) confocal images. The data in plot (b) were transformed by a Fourier low-pass filter.

The experimental steady-state flow patterns displayed high fidelity to the computational model conducted with identical boundary conditions (FIG. 2E). Further, the distribution of red color intensity was measured across the above six cross-sections for both simulated color maps and confocal images (FIG. 2F). The shape and relative magnitude of the intensity curves demonstrated a good agreement, and a comparable mixing efficacy to SL printed mixers was observed within the 13 mm long mixing channel.

Example 3

Fabrication and Characterization of Microfluidic-Integrated Salinity Sensor

Figure 3:
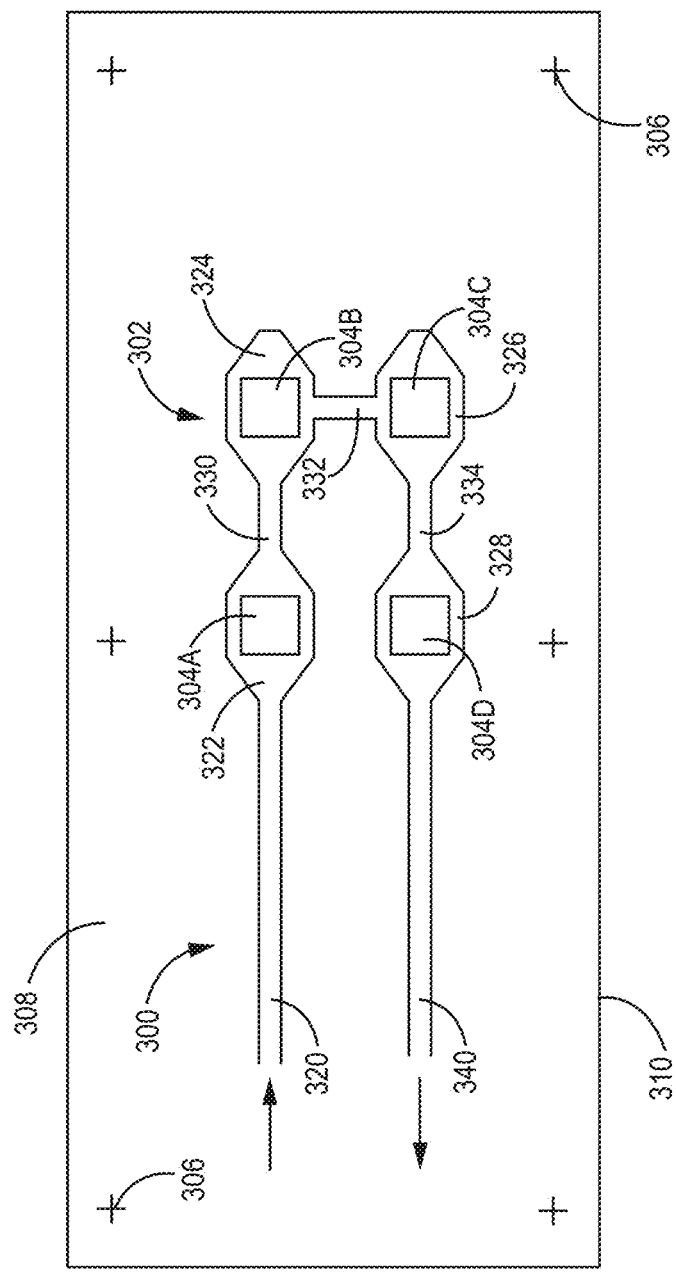
Figure 3A:
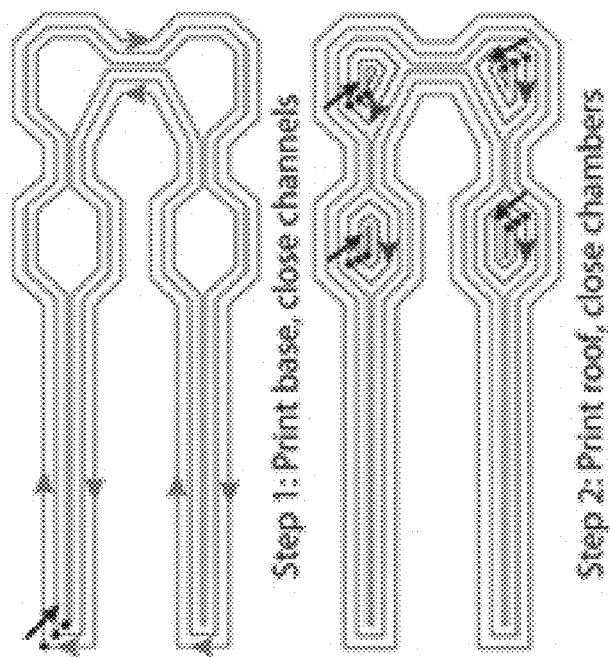
FIG. 3A is an overhead view of a layout of gold electrodes and alignment with microfluidic structures on the salinity sensor of Example 3, as well as a model of the measurement circuit. $C_{dl}$: double layer capacitance.

Microfluidic structures were directly printed on a microfabricated salinity sensor array as described in Example 1 above, realizing synchronous alignment and integration during the printing process. Gold electrodes and alignment marks were pe-deposited on a silicon wafer, and serially connected microfluidic channels and chambers were printed on top of the sensor array (FIG. 3A). Each salinity sensor consisted of a pair of gold electrodes that were housed inside the printed microfluidic chamber and used to measure the impedance of NaCl solutions flowing over the sensor. A simplified model of the measurement circuit included two double-layer capacitors and an equivalent parallel capacitor-resistor unit.

The salinity sensors were fabricated on 500 μm thick wafers that have an oxide layer of 300 nm (University Wafer, Inc., Boston, Mass.). Electrodes (10/190 nm Cr/Au, line width 100 μm, 60 μm separation within one channel) and alignment marks were deposited via standard photolithography procedures in the cleanroom. Before printing microfluidic structures, the sensor chips were cleaned by submerging in acetone, methanol, and isopropanol for 3 hours each, rinsing with DI water and blowing dry with high-purity N₂.

Prior to printing, the alignment marks were used to position the sensor array in the designed location within the coordinate system of the printer. During printing, the alignment marks were utilized to align the sensor chips with the coordinate system of the printer.

Figure 3B:
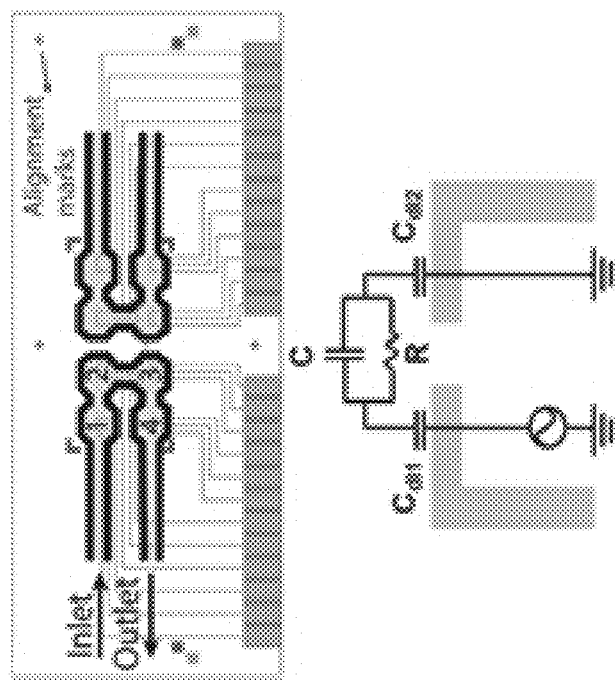
FIG. 3B is a schematic representation of a two-step printing procedure used to realize leakage free connections between self-supporting channels and chambers in the formation of the salinity sensor of Example 3.
Figure 3C:
FIG. 3C is an image of the microfluidic-integrated salinity sensor of Example 3 before connection to external tubes, with a scale bar of 5 mm.

Then the printing was conducted by extruding the silicone ink to construct the self-supporting microfluidic structures (FIG. 3B). Continuous printing toolpaths similar to the microfluidic mixers were designed. The base was first printed to close the lower channels and then the roofs were printed to close the remaining chambers. A robust adhesion formed between the substrate and printed parts after the RTV silicone cured under ambient conditions, creating a compact form-factor that guided the flow of analyte solutions on the sensors (FIG. 3C).

The completed salinity sensors were housed in a multi-electrode chip platform (ED-ME-CELL, MicruX Technologies, Napa, Calif.) which was connected to a mini USB box via an insulation-displacement contact cable, allowing each channel to be individually addressed.

Impedance measurements were then conducted with the hybrid microfabricated/3D printed salinity sensor. The impedance measurement of DI water and NaCl solutions was conducted on a semiconductor device analyzer (B1500A, Keysight Technologies, Inc.) as the sensor was flushed at a flow rate of 50 µL/min via a two-channel syringe pump (Model Fusion 100CR, Chemyx, Inc.). Real-time measurement of solution impedance was conducted at a frequency of 60 kHz.

Figure 3D:
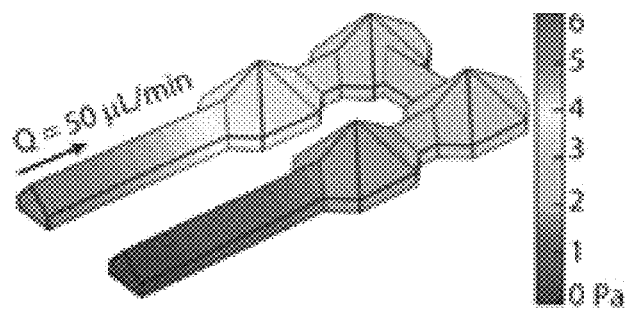
FIG. 3D is a computational fluid dynamics (CFD) simulated pressure distribution on the silicone wall under a flow rate of 50 μL/min for the salinity sensor of Example 3.

The microfluidic channels and chambers had a total internal volume of 20.87 µL, and a flow rate of 50 µL/min was used for the impedance measurement. CFD simulations showed highly laminar flow within the sensor and a back pressure of about 6 Pa (FIG. 3D) at the inlet, well below the burst pressure of the silicone structures. Therefore, the microfluidic-integrated sensor demonstrated good structural integrity and no leakage was observed during our tests.

Figure 3E:
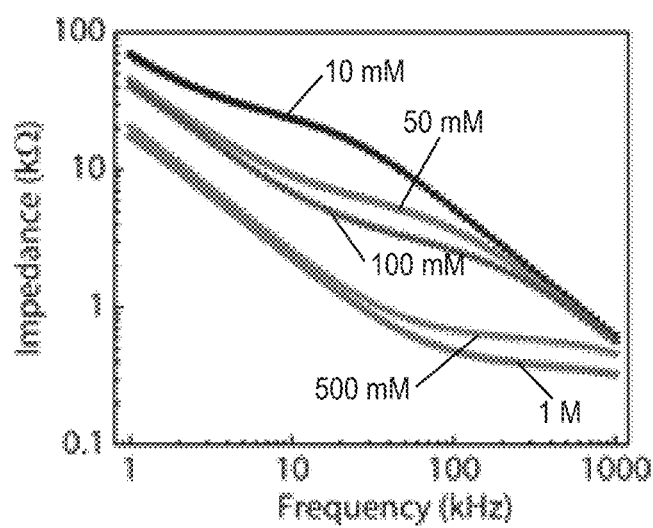
FIG. 3E is a plot of impedance spectra of different NaCl solutions measured with Sensor 1 from 1 to 1000 kHz (n=5) for the salinity sensor of Example 3.

AC signals were applied to the electrodes and frequency sweeps were conducted in the range of 1-1,000 kHz as NaCl solutions of different concentrations were flushed over the sensor. The acquired impedance spectra were in good agreement with the literature and high repeatability was observed for the four sensors in the tested array (FIG. 3E).

Figure 3F:
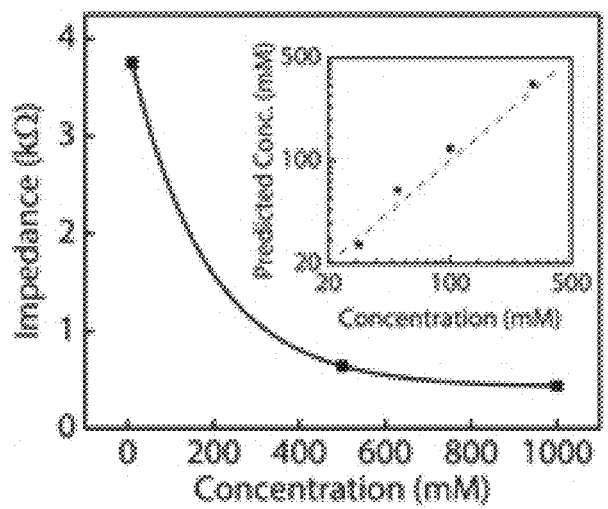
FIG. 3F is a calibration curve of the salinity sensor of Example 3 that was fitted with an exponential decay function. Inset plot displays the concentration prediction of four NaCl solutions with the salinity sensor. The impedance was measured at 145 kHz.

To utilize the device as a salinity sensor, Sensor 1 was calibrated with the measured impedance of NaCl solutions and found that the impedance-concentration relationship of NaCl solutions at 145 kHz could be fitted closely with the exponential decay equation:

$$Z = Ae^{(-c/t)} + Z_0$$

where Z is the impedance of the NaCl solutions measured at 145 kHz, c is the molar concentration of the solutions, and A, t and $Z_0$ are the fitted parameters (FIG. 3F).

Figure 3G:
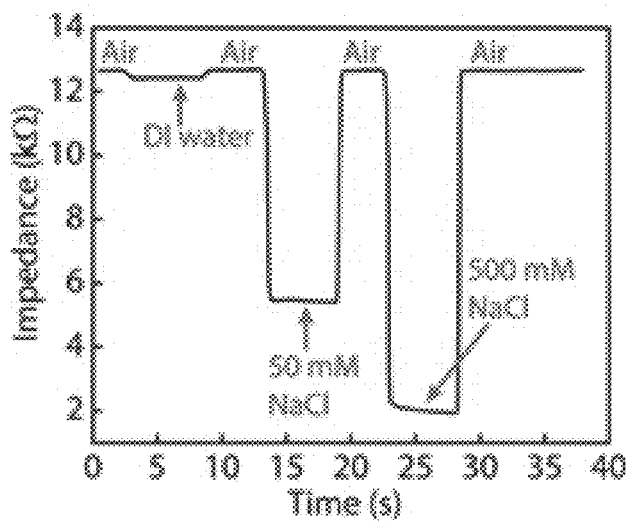
FIG. 3G is a plot of a real-time impedance measurement at 60 kHz of DI water, 50 and 500 mM NaCl solutions that were flowed through the salinity sensor of Example 3. The baseline denotes the impedance measured with an empty sensor.

With this model, accurate predictions of NaCl concentrations were obtained by the 3D printed salinity sensor. Real-time and dynamic salinity sensing is important for applications such as sea water purification and ocean environment monitoring. To demonstrate the real-time impedance measurement with the salinity sensor, deionized water, 50 mM and 500 mM NaCl solutions were sequentially flushed over the sensor with air gaps in between while the frequency was held at 60 kHz. Using the impedance measured at the air-filled state as the baseline, the impedance change induced by salt concentrations was clearly observed (FIG. 3G). The combination of microfabrication and 3D printing represents a compelling strategy for automatable production of biochemical sensors.

Example 4

Fabrication and Characterization of Microfluidic Valves and Pumps

With the extrusion-based 3D printing method, the self-supporting microfluidic structures can be readily applied to create functional microfluidic valves and pumps that are conformal to curvilinear surfaces via overlapping silicone channels and encapsulation (shown schematically FIG. 4A).

The microfluidic valves and pumps were fabricated by sequentially printing flow channels, control channels and an encapsulation container with silicone as described in Example 1 above. After the silicone structures were fully vulcanized, metal tubes were inserted into the control channels and the UV-curable resin was deposited in the encapsulation container, which was cured under 400 nm UV light for 5 min (available under the trade designation WF-501B CREE XR-C, UltraFire from Cree, Inc., Cary, N.C.).

As shown schematically in FIG. 4A, the 3D printed microfluidic valves consisted of one flow channel that permitted the liquid to traverse and one control channel that was conformally printed over the flow channel. An enclosed hollow space was thereby created between the two channels to act as a valve when actuated by pressurized gas.

The valve section, the crossing junction of the two channels, was then encapsulated and hardened by a UV-curable acrylate ester-based resin so that only downward expansion of the pressurized gas in the control channel was allowed to close the valve (FIG. 4B) The UV-curable resin, a blend of acrylate esters and amine-modified acrylate esters (available under the trade designation PRO-001 UV), was purchased from NovaCentrix, Austin, Tex.

The highly elastic silicone wall provided a flexible native membrane to open or close the valve. The control channel could be conveniently interfaced with external tubes and sealed directly with the encapsulation resin, which maintained its seal at an air pressure of up to 600 kPa. Generally, a higher flow pressure required a correspondingly higher closing pressure to stop the flow.

Figure 4C:
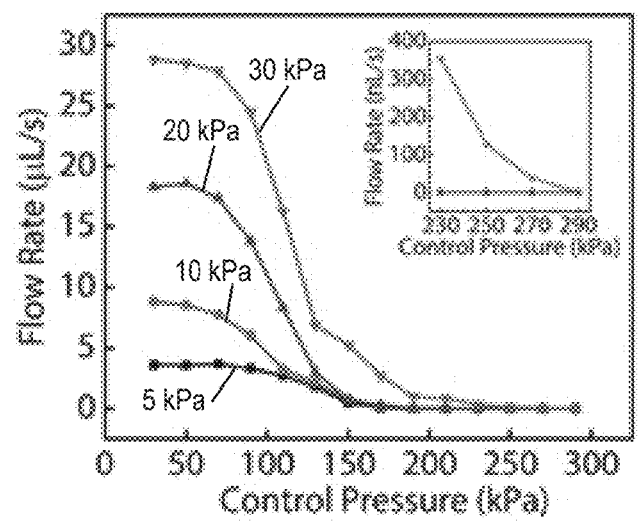
FIG. 4C is a plot of a closing pressure test of the 3D printed microfluidic valve of Example 4 under varying flow pressures.

For the closing pressure tests of the valve, a 300 kPa controlling pressure closed the valve completely while a hydraulic pressure up to 30 kPa was applied to the flow channel (FIG. 4C). Further, peristaltic microfluidic pumps can also be directly 3D printed using three controlling channels laid out in parallel and encapsulated as one unit. The microfluidic pump was operated by activating the control channels according a three-phase peristaltic code. Longer actuation times yielded a more complete shut-off of the control channels and therefore could be tuned to generate a higher pumping volume per cycle.

Figure 4D:
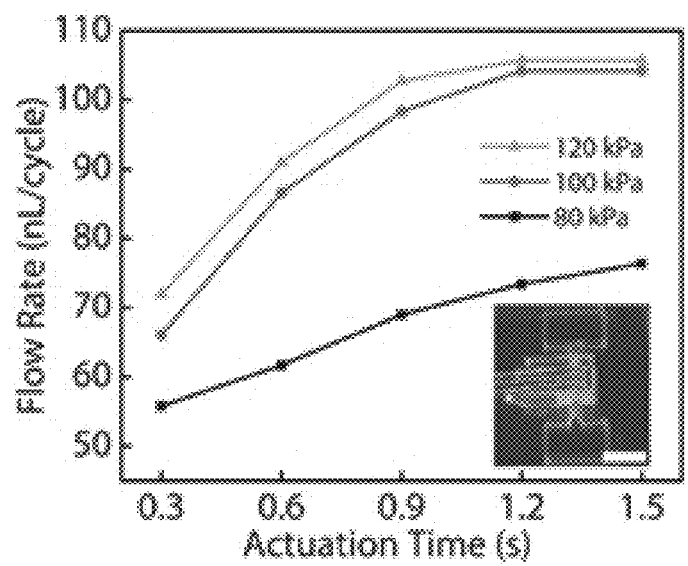
FIG. 4D is a plot of a flow rate test of a microfluidic pump utilized with the microfluidic valve of Example 4. The pump was actuated with a standard peristaltic code: 001, 100, 010, where 1 and 0 denote the open and closed state respectively. The inset image in FIG. 4D, which has a 5 mm scale bar, displays a 3D printed microfluidic pump with two liquid reservoirs.
Figure 4E:
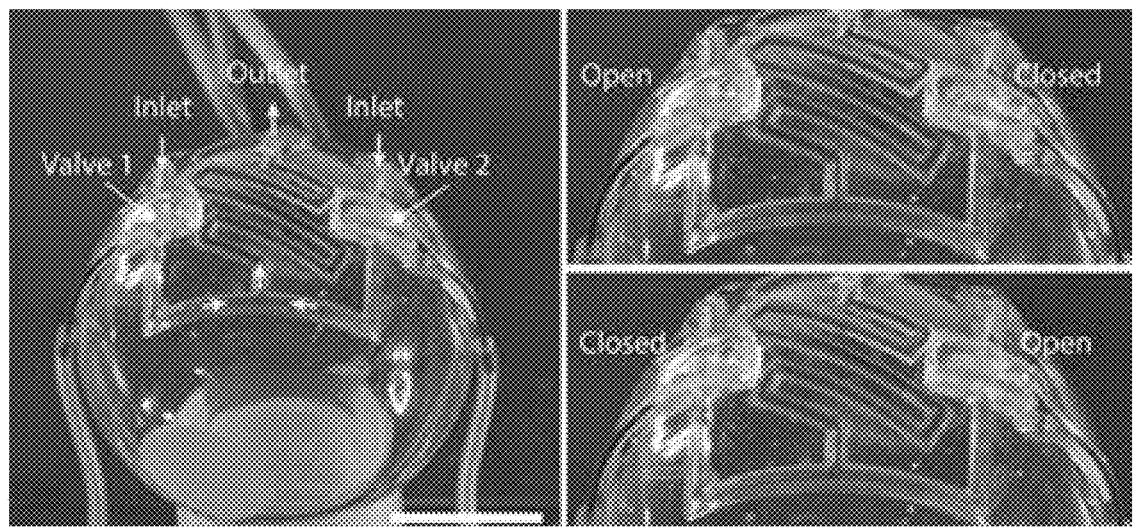
FIG. 4E includes photographs of 3D printed spherical converging and serpentine microfluidic channels with integrated valves according to Example 4, with a scale bar of 10 mm. The images show three combinational operation states of valves 1 and 2.

In one example, a flow rate of 105 µL/cycle was achieved with an actuation pressure of 100 kPa and an actuation time of 1.2 s (FIG. 4D). The flow rate of the microfluidic valve was measured via the mass of flowed solutions with a balance (available under the trade designation MS304S, Mettler Toledo, Inc., Columbus, Ohio). The pumping rate of the microfluidic pumps was measured by capturing video and measuring the traveling distance of the fluid within the transparent tubes.

Emerging microfluidics-based biomedical applications such as physiological status monitoring via sweat collection and sensing require the direct integration of microfluidic networks conformally onto curvilinear surfaces such as human skin. The high flexibility and stretchability of the 3D printed self-supporting structures provide a promising new avenue to next-generation wearable microfluidic devices. More importantly, spatially structured toolpaths allow us to transcend the conventional 2D microfluidic form factor and directly 'write' self-supporting microfluidic structures onto 3D targets.

Figure 4F:
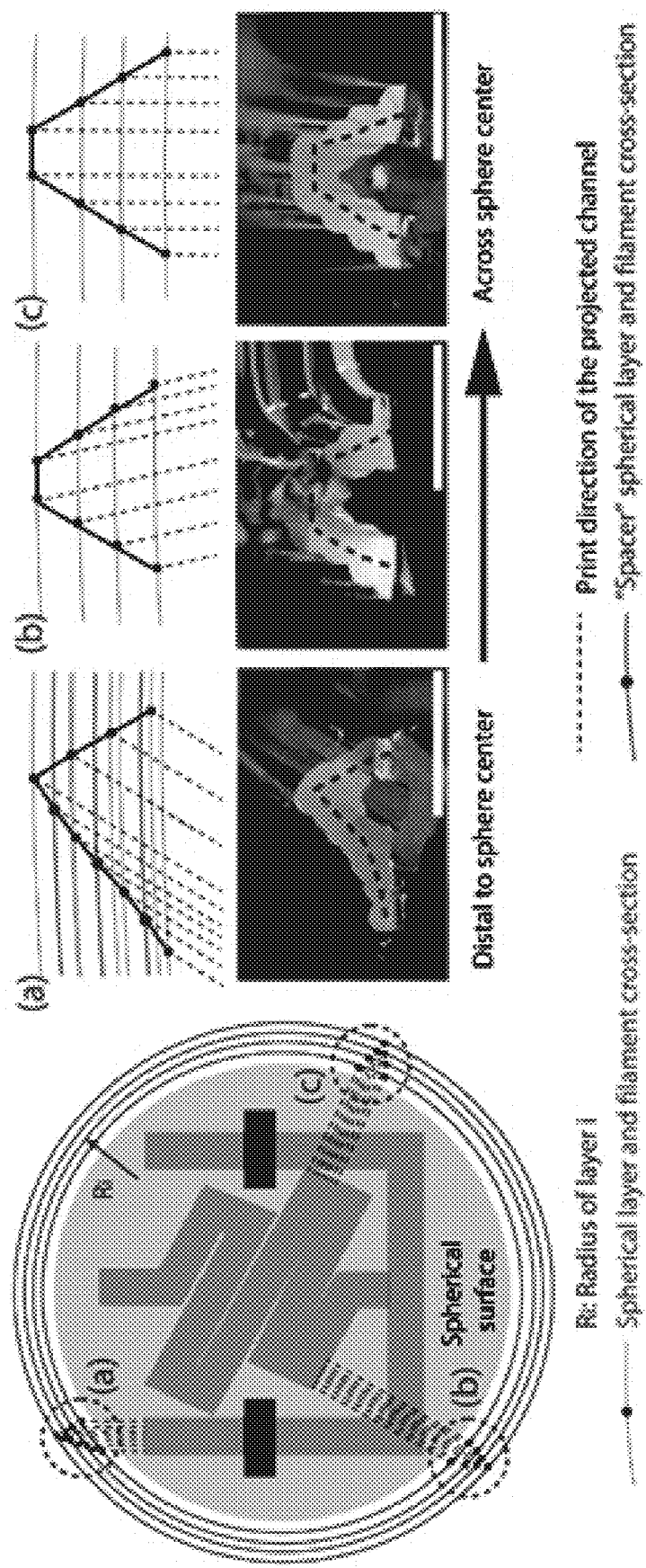
FIG. 4F displays a filament stacking schemes of spherical microfluidic channels, with a scale bar of 1 mm. Sub-panels (a)-(c) demonstrate the designed and printed profiles of three channel cross-sections. "Spacer" filaments were added to prevent the collapse of asymmetric channels that were distal to the sphere center.

Converging and serpentine microfluidic channels were designed and printed onto a spherical surface (the outer surface of a 10 mL glass flask) with simultaneously integrated valves (FIG. 4E) as described in Example 1 above. To generate the toolpaths of the 3D microfluidic network, the channel routes and valve structures were first projected onto a planar surface (FIG. 4F). The local cross-sectional profiles of the channels were then inspected by extending the individual filaments onto the corresponding spherical layers. The filament stacking schemes were specifically designed to ensure an even spacing between adjacent filaments. As the microfluidic channel was placed further away from the sphere center, the cross-sectional profile became less symmetric with the outer half being more extended. Therefore, extra 'spacer' filaments were needed to prevent the collapse and clogging of the channels (FIG. 4F (a)-(c)).

The cross-sectional profiles of the spherical microfluidic channels closely resemble the designed filament stacking schemes. Controlled by the two integrated valves, the liquid sources could be selected, either as a single input or the mixing of two inputs, to enter the serpentine channel and further guided to flow across the spherical surface.

Embodiments

Embodiment A. A printed structure comprising a plurality of overlying layers of elongate polymeric filaments stacked on a surface of a substrate, wherein the elongate polymeric filaments are stacked on each other along their lengths to form a liquid impermeable, self-supporting wall, and wherein the liquid impermeable self-supporting wall forms a wall angle of about 30° to about 90° with respect to a plane of the surface of the substrate.

Embodiment B. The printed structure of Embodiment A, wherein the elongate polymeric filaments are printed on the surface of the substrate in a substantially linear pattern when viewed along a direction normal to the surface of the substrate.

Embodiment C. The printed structure of Embodiments A to B, wherein the elongate polymeric filaments are printed on the surface of the substrate in a substantially circular pattern when viewed along a direction normal to the surface of the substrate.

Embodiment D. The printed structure of any of Embodiments A to C, wherein the filaments comprise an elastic polymeric material chosen from any of silicones, (meth)acrylates, polystyrene, biodegradable polymers, hydrogels, PEGDA, biocompatible polymers, thiolenes, and mixtures and combinations thereof.

Embodiment E The printed structure of Embodiment D, wherein the filaments comprise a silicone compound.

Embodiment F. The printed structure of Embodiment E, wherein the silicone compound comprises an acetoxy silicone compound curable at room temperature.

Embodiment G. The printed structure of any of Embodiments A to F, wherein the wall angle is greater than about 30°.

Embodiment H. The printed structure of any of Embodiments A to G, wherein the wall angle is greater than about 45°.

Embodiment I. The printed structure of any of Embodiments A to H, wherein the filaments are printed by extrusion.

Embodiment J. The printed structure of any of Embodiments a to I, wherein the wall has an overhang length of less than about 1 mm.

Embodiment K. The printed structure of any of Embodiments A to J, wherein the wall has an overhang length of less than about 750 microns.

Embodiment L. The printed structure of any of Embodiments A to K, wherein the substrate is substantially planar.

Embodiment M. The printed structure of any of Embodiments A to L, wherein the substrate is non-planar.

Embodiment N. The printed structure of any of Embodiments A to M, wherein the substrate is chosen from skin, tissue, organs, glass, textiles, clothing, insects, and animals.

Embodiment O. The printed structure of any of Embodiments A to N, wherein the substrate is an inorganic material.

Embodiment P. The printed structure of any of Embodiments A to O, wherein the substrate is an organic material.

Embodiment Q. The printed structure of Embodiment P, wherein the organic material is a flexible polymeric film.

Embodiment R. The printed structure of any of Embodiments A to Q, wherein the filaments further comprise ceramic particles, metal particles, and mixtures and combinations thereof.

Embodiment S. The printed structure of any of Embodiments A to R, wherein the filaments have a cross-sectional diameter of about 100 nm to about 500 µm.

Embodiment T. A printed structure comprising a plurality of overlying layers of elongate polymeric filaments stacked on a surface of a substrate, wherein the elongate polymeric filaments are stacked on each other along their lengths to form opposed liquid impermeable, self-supporting walls each having a wall angle of greater than about 30° with respect to a plane of the surface of the substrate, and wherein the opposed liquid impermeable walls merge in an apex region to form an enclosed fluid passage.

Embodiment U. The printed structure of Embodiment T, wherein the enclosed fluid passage has a substantially circular cross-sectional shape when viewed in a plane normal to the surface of the substrate.

Embodiment V. The printed structure of any of Embodiments T to U, wherein the enclosed fluid passage has a substantially square or substantially triangular cross-sectional shape when viewed in a plane normal to the surface of the substrate.

Embodiment W. The printed structure of any of Embodiments T to V, wherein the elongate polymeric filaments are printed on the surface of the substrate in a substantially linear pattern when viewed along a direction normal to the surface of the substrate.

Embodiment X. The printed structure of any of Embodiments T to W, wherein the elongate polymeric filaments are printed on the surface of the substrate in a substantially circular pattern when viewed along a direction normal to the surface of the substrate.

Embodiment Y. The printed structure of any of Embodiments T to X, wherein the filaments comprise a silicone compound.

Embodiment Z. The printed structure of Embodiment Y, wherein the filaments further comprise ceramic particles, metal particles, and mixtures and combinations thereof.

Embodiment AA. The printed structure of any of Embodiments Y to Z, wherein the silicone compound comprises an acetoxy silicone compound.

Embodiment BB. The printed structure of any of Embodiments T to AA, wherein the wall angle of each opposed wall is greater than about 37° as measured in a plane normal the plane of the substrate.

Embodiment CC. The printed structure of Embodiment BB, wherein the wall angle is greater than about 45°.

Embodiment DD. The printed structure of any of Embodiments T to CC, wherein each of the opposed walls has an overhang length of less than about 1 mm on the surface of the substrate.

Embodiment EE. The printed structure of any of Embodiments T to DD, wherein each of the opposed walls has an overhang length of less than about 750 microns on the surface of the substrate.

Embodiment FF. The printed structure of any of Embodiments T to EE, wherein the enclosed fluid passage has a width of greater than about 100 microns.

Embodiment GG. The printed structure of any of Embodiments T to FF, wherein each of the opposed walls has a thickness of greater than about 100 microns.

Embodiment HH. The printed structure of any of Embodiments T to GG, wherein the fluid passage has a burst pressure of greater than about 25 kPa.

Embodiment II. The printed structure of any of Embodiments T to HH, wherein the fluid passage has a burst pressure of greater than about 45 kPa.

Embodiment JJ. The printed structure of any of Embodiments T to II, wherein the substrate is substantially planar.

Embodiment KK. The printed structure of any of Embodiments T to JJ, wherein the substrate is non-planar.

Embodiment LL. The printed structure of any of Embodiments T to KK, wherein at least one of the opposed walls comprises a spacer filament.

Embodiment MM. A method of making a printed structure, the method comprising:
  extruding through a nozzle an elongate polymeric base filament in a pattern on a surface of a substrate, wherein the base filament has a length and a width; and
  moving the nozzle in a plane normal to a plane of the substrate to stepwise extrude and stack a plurality of polymeric filaments onto the base filament such that each of the polymeric filaments extruded onto the base filament contact one another along their lengths to form a wall with a wall angle of about 30° to about 90° with respect to the plane of the surface of the substrate.

Embodiment NN. The method of Embodiment MM, further comprising at least partially curing the wall to form a self-supporting wall on the surface of the substrate.

Embodiment OO. The method of any of Embodiments MM to NN, wherein the plurality of elongate polymeric filaments stacked on the base filament are each extruded in substantially parallel planes.

Embodiment PP. The method of Embodiment OO, wherein the elongate polymeric filaments are stacked on each other along their lengths such that the self-supporting wall is liquid impermeable.

Embodiment QQ. The method of any of Embodiments MM to PP, wherein the elongate polymeric filaments have a substantially circular cross-sectional shape.

Embodiment RR. The method of any of Embodiments MM to QQ, wherein the elongate polymeric filaments comprise a silicone compound.

Embodiment SS. A method of making a printed structure, the method comprising:
  extruding through a nozzle an elongate polymeric base filament in a pattern on a surface of a substrate, wherein the base filament has a length and a width;
  moving the nozzle in a first plane substantially normal to a plane of the substrate and a second plane substantially normal to the plane of the substrate to stepwise extrude and stack a plurality of polymeric filaments onto the base filament such that each of the polymeric filaments contact one another along their lengths to form opposed walls,
wherein each of the opposed walls forms a wall angle of about 30° to about 90° with respect to a plane of the surface of the substrate; and
moving the nozzle to extrude polymeric filaments to merge the walls to form an enclosed passage in the printed structure.

Embodiment TT. The method of Embodiment SS, further comprising at least partially curing the polymeric filaments to form a liquid-impermeable passage in the printed structure.

Embodiment UU. The method of Embodiment TT, wherein the enclosed fluid passage has a substantially circular cross-sectional shape when viewed in a plane normal to the surface of the substrate.

Embodiment VV. The method of any of Embodiments SS to UU, wherein the substrate is non-planar.

Embodiment WW. The method of any of Embodiments SS to VV, wherein the substrate is spherical.

Embodiment XX. The method of any of Embodiments SS to WW, wherein the elongate polymeric filaments comprise a silicone compound.

Embodiment YY. A microfluidic mixing device, the device comprising:
  a plurality of polymeric structures on a surface of a substrate, wherein the structures extend away from the surface of the substrate;
  a body, comprising:
an elongate polymeric base filament in a pattern on a surface of a substrate, wherein the base filament has a length and a width, and wherein a first portion the base filament at least partially bounds the plurality of polymeric structures,
  a plurality of polymeric filaments stacked onto the base filament such that each of the polymeric filaments contact one another along their lengths to form opposed first and second walls, wherein each of the first and the second opposed walls forms a wall angle of about 35° to about 90° with respect to a plane of the surface of the substrate, and
a roof to connect the opposed first and second walls to form an enclosed fluid passage bounded by the opposed walls and the roof, wherein the fluid passage comprises therewithin the plurality of structures.

Embodiment ZZ. The microfluidic mixer of Embodiment YY, wherein the walls are liquid impermeable.

Embodiment AAA. The microfluidic mixer of any of Embodiments YY to ZZ, wherein the structures comprise a first polymeric material and the polymeric filaments comprise a second polymeric material different from the first polymeric material.

Embodiment BBB. The microfluidic mixer of any of Embodiments YY to AAA, wherein the structures comprise polycaprolactone and the filaments comprise a silicone compound.

Embodiment CCC. The microfluidic mixer of any of Embodiments YY to BBB, wherein the pattern further comprises a second inlet portion connected to and substantially normal to the first portion and a third outlet portion connected to the first portion.

Embodiment DDD. The microfluidic mixer of any of Embodiments YY to CCC, wherein the polymeric structures comprise ridges with an angled shape.

Embodiment EEE. The microfluidic mixer of Embodiment DDD, wherein a first portion of the ridges each have a long portion proximal a first wall and a short portion proximal a second wall, and a second portion of the polymeric ridges each have a long portion proximal the second wall and a short portion proximal the first wall.

Embodiment FFF. The microfluidic mixer of Embodiment EEE, wherein the polymeric ridges are arranged in a herringbone pattern.

Embodiment GGG. The microfluidic mixer of Embodiment GGG, wherein the herringbone pattern comprises a regular herringbone pattern.

Embodiment HHH. A method for making a microfluidic mixing device, the method comprising:
  printing a plurality of polymeric structures on a surface of a substrate, wherein the structures extend away from the surface;
  printing an elongate polymeric base filament in a pattern on a surface of a substrate, wherein the base filament has a length and a width, and wherein a first portion the base filament at least partially bounds the plurality of polymeric structures;
  stacking a plurality of polymeric filaments onto the first portion of the base filament such that each of the polymeric filaments contact one another along their lengths to form opposed first and second walls, wherein each of the first and the second opposed walls forms a wall angle of about 35° to about 90° with respect to a plane of the surface of the substrate; and
printing a roof to connect the opposed first and second walls to form an enclosed fluid passage bounded by the opposed walls and the roof, wherein the fluid passage comprises therewithin the plurality of structures.

Embodiment III. The method of Embodiment HHH, further comprising at least partially curing the polymeric filaments to form opposed self-supporting walls and a liquid impermeable passage bounded by the opposed self-supporting walls.

Embodiment JJJ. The method of any of Embodiments HHH to III, wherein the structures comprise a first polymeric material and the polymeric filaments comprise a second polymeric material different from the first polymeric material.

Embodiment KKK. The method of any of Embodiments HHH to JJJ, wherein the structures comprise polycaprolactone and the filaments comprise a silicone compound.

Embodiment LLL. The method of any of Embodiments HHH to KKK, wherein the pattern further comprises a second inlet portion connected to and substantially normal to the first portion and a third outlet portion connected to the first portion.

Embodiment MMM. The method of any of Embodiments HHH to LLL, wherein the polymeric structures comprise ridges with an angled shape.

Embodiment NNN. The method of Embodiment MMM, wherein a first portion of the ridges each have a long portion proximal a first wall and a short portion proximal a second wall, and a second portion of the polymeric ridges each have a long portion proximal the second wall and a short portion proximal the first wall.

Embodiment OOO. The method of any of Embodiments MMM to NNN, wherein the polymeric ridges are arranged in a herringbone pattern.

Embodiment PPP. The method of Embodiment OOO, wherein the herringbone pattern comprises a regular herringbone pattern.

Embodiment QQQ. A sensor system, comprising:
  a substrate comprising a sensor; and
  a printed structure comprising a plurality of overlying layers of elongate polymeric filaments stacked on a surface of the substrate proximal the sensor, wherein the elongate polymeric filaments are stacked on each other along their lengths to form opposed liquid impermeable walls each having a wall angle of greater than about 30° with respect to a plane of the surface of the substrate, and wherein the opposed liquid impermeable walls merge in an apex region to form an enclosed fluid passage, and wherein the fluid passage is in fluid communication with the sensor.

Embodiment RRR. The sensor system of Embodiment QQQ, wherein the sensor comprises an electrode, and the printed structure overlies at least a portion of the electrode.

Embodiment SSS. The sensor system of any of Embodiments QQQ to RRR, wherein the enclosed fluid passage comprises an inlet, an outlet, and an arrangement of chambers between the inlet and the outlet, and wherein at least one of the chambers bounds the electrode.

Embodiment TTT. The sensor system of Embodiment SSS, wherein the chambers have a pyramidal shape.

Embodiment UUU. The sensor system of any of Embodiments SSS to TTT, wherein the inlet and the outlet are connected to external tubes to provide a flow of a fluid through the chambers.

Embodiment VVV. The sensor system of any of Embodiments QQQ to UUU, wherein the sensor comprises a biochemical sensor.

Embodiment WWW. The sensor system of any of Embodiments QQQ to VVV, wherein the sensor comprises a salinity sensor.

Embodiment XXX. The sensor system of any of Embodiments QQQ to WWW, wherein the fluid passage is aligned with the sensor with a precision of at least 100 nm.

Embodiment YYY. A method for making a sensor system, the method comprising:
  printing an elongate polymeric base filament in a pattern on the surface of a substrate, wherein the surface of the substrate comprises a sensor with at least one electrode, wherein the base filament has a length and a width, and wherein a first portion the base filament at least partially bounds the sensor;
  stacking a plurality of polymeric filaments onto the first portion of the base filament such that each of the polymeric filaments contact one another along their lengths to form opposed first and second walls, wherein each of the first and the second opposed walls forms a wall angle of about 30° to about 90° with respect to a plane of the surface of the substrate; and
printing a roof to connect the opposed first and second walls to form an enclosed fluid passage bounded by the opposed walls and the roof, wherein the fluid passage at least partially overlies the at least one electrode of the sensor.

Embodiment ZZZ. The method of Embodiment YYY, further comprising at least partially curing the polymeric filaments to form opposed first and second self-supporting walls on the substrate.

Embodiment AAAA. The method of any of Embodiments YYY to ZZZ, wherein the enclosed fluid passage comprises an inlet, an outlet, and an arrangement of chambers between the inlet and the outlet, and wherein at least one of the chambers bounds the electrode.

Embodiment BBBB. The method of Embodiment AAAA, wherein the chambers have a pyramidal shape.

Embodiment CCCC. The method of any of Embodiments AAAA to BBBB, further comprising connecting external tubes to the inlet and the outlet to provide a flow of a fluid through the chambers.

Embodiment DDDD. The method of any of Embodiments YYY to CCCC, wherein the sensor comprises a biochemical sensor.

Embodiment EEEE. The method of Embodiment DDDD, wherein the sensor comprises a salinity sensor.

Embodiment FFFF. The method of any of Embodiments YYY to EEEE, wherein the substrate comprises a biological surface.

Embodiment GGGG. The method of Embodiment FFFF, wherein the biological surface is human skin.

Embodiment HHHH. The method of any of Embodiments YYY to GGGG, wherein the substrate comprises a plurality of sensors, and an arrangement of fluid passages overlying the sensors, the method further comprising directing fluid through the arrangement of fluid passages to selectively activate one or more of the plurality of sensors.

Embodiment IIII. A valve, comprising:
a flow channel comprising a plurality of overlying layers of elongate polymeric filaments stacked on a surface of a substrate, wherein the elongate polymeric filaments are stacked on each other along their lengths to form opposed liquid impermeable walls each having a wall angle of greater than about 35° with respect to a plane of the surface of the substrate, and wherein the opposed liquid impermeable walls merge in an apex region to form an enclosed fluid passage;
a control channel comprising a plurality of overlying layers of elongate polymeric filaments stacked on each other along their lengths to form opposed liquid impermeable walls each having a wall angle of greater than about 35° with respect to a plane of the surface of the substrate, wherein the opposed liquid impermeable walls merge in an apex region to form an enclosed passage, and wherein the control channel comprises a first portion on the surface of the substrate and a second portion that overlies the flow channel and forms an enclosed valve portion therebetween; and
an encapsulant structure overlying the valve portion.

Embodiment JJJJ. The valve of Embodiment IIII, wherein the encapsulant structure extends over at least a part of the first portion of the control channel.

Embodiment KKKK. The valve of any of Embodiments IIII to JJJJ, wherein the control channel is interfaced with an external tube to pneumatically control the valve portion.

Embodiment LLLL. The valve of any of Embodiments IIII to KKKK, wherein the substrate is substantially planar.

Embodiment MMMM. The valve of any of Embodiments IIII to LLLL, wherein the substrate is non-planar.

Embodiment NNNN. The valve of any of Embodiments IIII to MMMM, wherein the substrate is spherical.

Embodiment OOOO. The valve of any of Embodiments IIII to NNNN, wherein the substrate is a biological surface.

Embodiment PPPP The valve of Embodiment OOOO, wherein the biological surface is human skin.

Embodiment QQQQ. The valve of any of Embodiments IIII to PPPP, wherein the elongate polymeric filaments of the flow channel and the control channel comprise a first polymeric material, and the encapsulant structure comprises a second polymeric material different from the first polymeric material.

Embodiment RRRR. The valve of Embodiment QQQQ, wherein the first polymeric material comprises a silicone and the second polymeric material comprises an acrylate ester-based resin.

Embodiment SSSS. The valve of Embodiment RRRR, wherein the first polymeric material is curable at room temperature and the second polymeric material is curable with UV.

Embodiment TTTT. The valve of any of Embodiments IIII to SSSS, wherein the encapsulant structure encloses the valve portion.

Embodiment UUUU. The valve of any of Embodiments IIII to TTTT, wherein the substrate comprises a plurality of sensors, and enclosed fluid passage overlies the plurality of sensors, and wherein the valve is configured to direct a fluid flow through the enclosed fluid passage to a selected sensor or a combination of sensors in the plurality of sensors.

Embodiment VVVV. A three-dimensional printing system, the system comprising:
an extruder that extrudes a polymeric material, wherein the extruder comprises a nozzle moved in response to instructions from a controller, and wherein the nozzle is configured to:
move along a surface of a substrate to extrude an elongate polymeric base filament in a pattern on the surface of a substrate;
move in a first plane substantially normal to a plane of the substrate and a second plane substantially normal to the plane of the substrate to stepwise form and stack a plurality of polymeric filaments onto the base filament such that each of the polymeric filaments contact one another along their lengths to form opposed walls, wherein each of the opposed walls forms a wall angle of about 30° to about 90° with respect to a plane of the surface of the substrate; and
move in a region between the opposed walls to merge the walls to form a printed structure comprising an enclosed passage.

Various embodiments of the invention have been described. These and other embodiments are within the scope of the following claims.

The invention claimed is:

1. A printed structure comprising a plurality of overlying layers of elongate polymeric filaments stacked on a surface of a substrate, wherein the elongate polymeric filaments are stacked on each other along their lengths to form a liquid impermeable, self-supporting wall, wherein the liquid impermeable self-supporting wall forms a wall angle of about 30° to about 90° with respect to a plane of the surface of the substrate, and wherein the liquid impermeable self-supporting wall has a thickness of a cross-section of a single elongate polymeric filament of the elongate polymeric filaments stacked to form the liquid impermeable self-supporting wall.

2. The printed structure of claim 1, wherein the elongate polymeric filaments are printed on the surface of the substrate in a substantially linear pattern when viewed along a direction normal to the surface of the substrate.

3. The printed structure of claim 1, wherein the elongate polymeric filaments are printed on the surface of the substrate in a substantially circular pattern when viewed along a direction normal to the surface of the substrate.

4. The printed structure of claim 1, wherein the elongate polymeric filaments comprise an elastic polymeric material chosen from any of silicones, (meth)acrylates, polystyrene, biodegradable polymers, hydrogels, PEGDA, biocompatible polymers, thiolenes, and mixtures and combinations thereof.

5. The printed structure of claim 4, wherein the elongate polymeric filaments comprise a silicone compound.

6. The printed structure of claim 5, wherein the silicone compound comprises an acetoxy silicone compound curable at room temperature.

7. The printed structure of claim 1, wherein the wall angle is greater than about 30°.

8. The printed structure of claim 1, wherein the elongate polymeric filaments are printed by extrusion.

9. The printed structure of claim 1, wherein the liquid impermeable self-supporting wall has an overhang length of less than about 1 mm.

10. The printed structure of claim 1, wherein the substrate is non-planar.

11. The printed structure of claim 1, wherein the substrate is chosen from skin, tissue, organs, glass, textiles, clothing, insects, and animals.

12. The printed structure of claim 1, wherein the elongate polymeric filaments further comprise ceramic particles, metal particles, and mixtures and combinations thereof.

13. The printed structure of claim 1, wherein the liquid impermeable self-supporting wall is a first liquid impermeable self-supporting wall, wherein the printed structure further comprises a second liquid impermeable self-supporting wall on the surface of the substrate and opposite of the first liquid impermeable self-supporting wall, and wherein the first liquid impermeable self-supporting wall and the second liquid impermeable self-supporting wall merge in an apex region above the substrate to form an enclosed fluid passage.

14. The printed structure of claim 13, wherein the fluid passage has a burst pressure of greater than about 25 kPa.

15. The printed structure of claim 13, wherein at least one of the first liquid impermeable self-supporting wall or second liquid impermeable self-supporting wall comprises a spacer filament.

16. A method of making a printed structure, the method comprising:
  extruding through a nozzle an elongate polymeric base filament in a pattern on a surface of a substrate, wherein the base filament has a length and a width;
  moving the nozzle in a plane normal to a plane of the substrate to stepwise extrude and stack a plurality of polymeric filaments onto the base filament such that each of the polymeric filaments extruded onto the base filament contact one another along their lengths to form a wall with a wall angle of about 30° to about 90° with respect to the plane of the surface of the substrate, wherein the wall has a thickness of a cross-section of a single polymeric filament of the polymeric filaments stacked to form the wall; and
  at least partially curing the wall to form a liquid impermeable self-supporting wall on the surface of the substrate.

17. The method of claim 16, further comprising moving the nozzle to extrude polymeric filaments to merge the walls to form an enclosed passage in the printed structure.

18. The method of claim 16, wherein the substrate is non-planar.

19. The method of claim 16, wherein the polymeric filaments comprise a silicone compound.

* * * * *